United States Patent
Otsuka

(10) Patent No.: US 9,354,210 B2
(45) Date of Patent: May 31, 2016

(54) PLATE-TYPE CAPILLARY COLUMN, CAPILLARY COLUMN UNIT, AND CHROMATOGRAPH USING SAME

(75) Inventor: Takahiro Otsuka, Kyoto (JP)

(73) Assignee: HORIBA STEC, CO., LTD., Kyoto (JP)

( * ) Notice: Subject to any disclaimer, the term of this patent is extended or adjusted under 35 U.S.C. 154(b) by 26 days.

(21) Appl. No.: 14/233,490

(22) PCT Filed: Aug. 3, 2012

(86) PCT No.: PCT/JP2012/069893
§ 371 (c)(1),
(2), (4) Date: Jan. 17, 2014

(87) PCT Pub. No.: WO2013/018903
PCT Pub. Date: Feb. 7, 2013

(65) Prior Publication Data
US 2014/0165841 A1    Jun. 19, 2014

(30) Foreign Application Priority Data
Aug. 4, 2011   (JP) ................................. 2011-171301

(51) Int. Cl.
*G01N 30/60*  (2006.01)
*B01D 53/02*  (2006.01)
(Continued)

(52) U.S. Cl.
CPC ............ *G01N 30/606* (2013.01); *B01D 53/025* (2013.01); *G01N 30/467* (2013.01);
(Continued)

(58) Field of Classification Search
CPC ... G01N 30/467; G01N 30/468; G01N 30/60; G01N 30/6039; G01N 30/6052; G01N 30/606; G01N 30/6091; G01N 30/6095; G01N 2030/6056; G01N 2030/8881; B01D 53/025
See application file for complete search history.

(56) References Cited

U.S. PATENT DOCUMENTS

| 3,149,941 A | 9/1964 | Barnitz et al. |
| 3,254,479 A | 6/1966 | Doeschl |

(Continued)

FOREIGN PATENT DOCUMENTS

| CN | 102004137 | 4/2011 |
| EP | 1489045 | 12/2004 |

(Continued)

OTHER PUBLICATIONS

European Search Report for European Patent application No. 12819752.2, mail date Feb. 2, 2015.

(Continued)

*Primary Examiner* — Robert Clemente
(74) *Attorney, Agent, or Firm* — Greenblum & Bernstein, P.L.C.

(57) ABSTRACT

A plate-type capillary column has extensibility that enables a capillary to be extended as a whole to improve resolution of a chromatograph by stacking respective plate-type capillary columns. The capillary column is provided with a plate having first and second face plate parts that face each other; a capillary that is formed inside the plate; a first bottom-equipped hole connected to one end part of the capillary and formed to open in the first face plate part; and a second bottom-equipped hole connected to the other end part and formed to open in the second face plate part, wherein as viewed from a direction vertical to the first face plate part or the second face plate part, on a capillary column first virtual circle, passing through the second bottom-equipped hole, one or more through-holes penetrating through the first face plate part and the second face plate part are formed.

17 Claims, 15 Drawing Sheets

(a)

(b)

(51) Int. Cl.
*G01N 30/46* (2006.01)
*G01N 30/88* (2006.01)

(52) U.S. Cl.
CPC .......... *G01N30/6095* (2013.01); *G01N 30/468* (2013.01); *G01N 30/6039* (2013.01); *G01N 2030/8881* (2013.01)

(56) References Cited

U.S. PATENT DOCUMENTS

| | | | |
|---|---|---|---|
| 4,935,040 | A | 6/1990 | Goedert |
| 5,583,281 | A | 12/1996 | Yu |
| 5,690,763 | A | 11/1997 | Ashmead et al. |
| 6,699,392 | B1 | 3/2004 | Manginell et al. |
| 7,273,517 | B1 | 9/2007 | Lewis et al. |
| 2007/0017869 | A1 | 1/2007 | Goodley |
| 2009/0272270 | A1 | 11/2009 | McGill et al. |

FOREIGN PATENT DOCUMENTS

| | | |
|---|---|---|
| JP | 60-142254 | 7/1985 |
| JP | 61-288154 | 12/1986 |
| JP | 62-087858 | 4/1987 |
| JP | 5-180821 | 7/1993 |
| JP | 2006-90813 | 4/2006 |
| JP | 2007-033442 | 2/2007 |
| WO | 01/41931 | 6/2001 |
| WO | 2011/044350 | 4/2011 |

OTHER PUBLICATIONS

International Search Report in PCT/JP2012/069893, issued Oct. 2, 2012 including English language version.
China Office action in CN 201280011208.2, dated Oct. 30, 2014 along with an English translation thereof.
Japanese Office Action issued in Japanese application No. 2013-526971.

(a)

(b)

(a)

(b)

(a)

(b)

(a)

(b)

PLATE-TYPE CAPILLARY COLUMN, CAPILLARY COLUMN UNIT, AND CHROMATOGRAPH USING SAME

TECHNICAL FIELD

The present invention relates to a plate-type capillary column used for a chromatograph, and a capillary column unit using the plate-type capillary column.

BACKGROUND ART

As a capillary column used for a chromatograph, for example, one configured by winding a long and narrow glass tube in a coil shape is well known. In recent years, as a substitute for a large capillary column as described above, there has been proposed a plate-type capillary column moldable into a small shape, in which a groove is formed on a front surface of a glass plate.

More specifically, as illustrated in FIG. 1 of Patent Literature 1, there is a capillary column that is formed in a plate shape by, on some virtual plane, spirally winding a narrow tube, and also sandwiching the virtual plane between two flat circular plates from both sides. Also, this plate-type capillary column is provided with: a sample introduction port that is formed by making a bottom-equipped hole from a front side of the plate such that the bottom-equipped hole passes through an outer end of the spirally wound narrow tube; and a sample outlet port that is formed by making a bottom-equipped hole from the front side of the plate such that the bottom-equipped hole passes through an inner end of the narrow tube. That is, in the plate-type capillary column described in Patent Literature 1, the bottom-equipped holes opening on the same side with respect to a face plate part of the plate form the sample introduction port and the sample outlet port, respectively.

The plate-type capillary column described in Patent Literature 1 is only assumed to be used by itself; however, for example, for the purpose of improving resolution or the like by increasing a distance that fluid flows, plate-type capillary columns may be stacked.

A plate-type capillary column described in Patent Literature 2 is one configured such that on a front surface of one quartz glass plate, a groove is formed in a single stroke shape, and the groove serves as a capillary in a state where another plate-type capillary column is stacked with a back surface of the another plate-type capillary column facing to the front surface. Also, in order to be able to communicatively connect the capillaries of the respective plate-type capillary columns to make an extension by the stacking, two types of plate-type capillary columns are manufactured as illustrated in FIGS. 6 and 7 of Patent Literature 2.

More specifically, in a plate-type capillary column of a first type in Patent Literature 2, at an outer end of a capillary, a through-hole is formed so as to penetrate between front and back surfaces of a plate, and also, at an inner end of the capillary, a bottom-equipped hole that opens only on the front surface of the plate is formed. On the other hand, in a plate-type capillary column of a second type, although a shape of a capillary is the same as that of the first type, at an outer end of the capillary, a bottom-equipped hole that opens only on a front surface of a plate is formed, and at an inner end of the capillary, a through-hole that penetrates between the front and back surfaces of the plate is formed.

That is, regarding the plate-type capillary column described in Patent Literature 2, the two types of plate-type capillary columns respectively having different shapes are prepared, and by alternately stacking them, a capillary as a whole can be finally extended by the stacking.

However, having to manufacture the two types of plate-type capillary columns respectively having different shapes as described becomes a factor pushing up manufacturing cost correspondingly. Further, the plate-type capillary column described in each of Patent Literatures 1 and 2 is not assumed to be compatible with a measuring method that requires a complicated flow path for a backflush, heartcutting, or the like used in a chromatograph provided with a conventional capillary column using a glass tube. For this reason, making replacement from the capillary column using the glass tube to the plate-type capillary column is difficult in practice.

CITATION LIST

Patent Literature

Patent Literature 1: JP-A-Hei 5-180821
Patent Literature 2: JP-A-2006-90813

SUMMARY OF INVENTION

Technical Problem

The present invention is made in consideration of the problems as described above, and intended to provide a plate-type capillary column having extensibility that, even in the case of preparing only one type of shape, enables a capillary to be extended as a whole to improve resolution of a chromatograph by stacking respective plate-type capillary columns, and also a measuring method, which in the past, the plate-type capillary column has been difficult to cope with because a complicated flow path is required, to be realized, and also provide a capillary column unit or chromatograph using the plate-type capillary columns.

Solution to Problem

That is, a plate-type capillary column of the present invention is provided with: a plate having a first face plate part and a second face plate part that face to each other; a capillary that is formed inside the plate; a first bottom-equipped hole that is connected to one end part of the capillary and formed so as to open in the first face plate part; and a second bottom-equipped hole that is connected to the other end part of the capillary and formed so as to open in the second face plate part, wherein as viewed from a direction vertical to the first face plate part or the second face plate part, on a capillary column first virtual circle, one or more through-holes penetrating through the first face plate part and the second face plate part are formed, the circumference passing through the second bottom-equipped hole. Note that the capillary formed inside the plate refers to one that is, for example, formed such that a lateral face part of the capillary does not open to outer air, or the lateral face part is sealed not to come into contact with outer air.

If so, the first bottom-equipped hole opens in the first face plate part, and the second bottom-equipped hole opens in the second face plate part, so that by preparing a plurality of plate-type capillary columns having the same shape, and communicatively connecting the first bottom-equipped holes of the respective plate-type capillary columns to each other with the first face plate parts facing to each other, or communicatively connecting the second bottom-equipped holes to each other with the second face plate parts facing to each other, a capillary having an arbitrary length as a whole can be easily formed.

In other words, only by preparing the plurality of plate-type capillary columns having the same shape, and when stacking them in the direction vertical to the respective face plate parts, stacking them with alternately reversing a relative location between the face plate parts of each of the plate-type capillary columns, the length of the capillary as a whole can be freely adjusted. In addition, even though the length of the capillary can be freely changed, the shape of the plate-type capillary column can be limited to one type of shape, and therefore manufacturing cost can be significantly reduced. To describe more specifically, it is only necessary to manufacture one type of plate-type capillary column, so that it is only necessary to constantly form capillaries having the same shape, and therefore a working process taking time and effort, such as applying a liquid phase inside the capillaries, can be limited to one type of process to reduce the manufacturing cost.

Further, only by stacking the respective plate-type capillary columns in the direction vertical to the respective face plate parts, the length of the capillary as a whole can be easily adjusted, and therefore structure for realizing a measuring method for heartcutting, a backflush, or the like, which requires a complicated flow path, can be easily added to the plate-type capillary column.

Also, as viewed from the direction vertical to the first face plate part or the second face plate part, on the circumference of the capillary column first virtual circle, which passes through the second bottom-equipped hole, the one or more through-holes penetrating through the first face plate part and the second face plate part are formed, and therefore the through-holes can be used to form capillary branching for enabling the measuring method for heartcutting, backflush, or the like, which requires a complicated flow path.

As a specific position of the first bottom-equipped hole, which enables a length of capillary to be freely changed as a whole on the basis of a simple configuration and only a single type of capillary column, and a complicated flow path for heartcutting or a backflush to be configured by stacking, as viewed from the direction vertical to the first face plate part or the second face plate part, the first bottom equipped hole is present at a virtual center of the capillary column first virtual circle.

Other aspects of the first bottom-equipped hole for, similarly to the above-described plate-type capillary column, only by preparing one type of plate-type capillary column, enabling a length of a capillary to be easily changed as a whole by stacking, and a complicated flow path used for a special measuring method to be formed include one where as viewed from the direction vertical to the first face plate part or the second face plate part, the first bottom-equipped hole is present on the capillary column first virtual circle.

In order to, in the case of stacking the plate-type capillary columns with alternately reversing a relative location between the face plate parts of each of the plate-type capillary columns, make it possible to easily form another flow path so as to be able to introduce fluid from some plate-type capillary column into an immediately upper plate-type capillary column and also directly flow the fluid into, across one more upper capillary column, two more upper plate-type capillary column, it is only necessary that the second bottom-equipped hole and the respective through-holes are arranged so as to be rotational symmetric around the virtual center. If so, only by rotating, of the plate-type capillary columns stacked with the second face plate parts facing to each other, one plate-type capillary column around a central axis that passes through the first bottom-equipped hole and is vertical to the respective face plate parts, which of the second bottom-equipped hole and through-holes of the other plate-type capillary column the second bottom-equipped hole of the one plate-type capillary column is communicatively connected to can be appropriately selected. Accordingly, which of the holes of the stacked plate-type capillary column the capillary of the one plate-type capillary column is connected to can be appropriately selected, and therefore a complicated flow path for performing a measuring method for, for example, heartcutting, a backflush, or the like can be easily formed.

In order to easily form the capillary inside the plate-type capillary column, it is only necessary that the plate includes: a first plate element of which a front surface is formed with a groove; and a second plate element that is attached so as to cover the front surface of the first plate element. If so, by lidding the groove of the first plate element with the second plate element, the capillary can be easily formed inside the plate.

In order to further increase a degree of freedom of a flow path configuration in the case of stacking the plate-type capillary columns, it is only necessary that as viewed from the direction vertical to the first face plate part or the second face plate part, on a capillary column second virtual circle that is a circle concentric with the capillary column first virtual circle, one or more through-holes penetrating through the first face plate part and the second face plate part are further formed.

In order to, even in the case of further providing the one or more through-holes on the circumference of the capillary second virtual circle, make it difficult to cause interference with the capillary in terms of arrangement, and make it easy to design a length of the capillary as long as possible, it is only necessary that as viewed from the direction vertical to the first face plate part or the second face plate part, the first bottom-equipped hole, the second bottom-equipped hole, and the through-holes on the circumference of the capillary column first virtual circle, and the through-holes on the circumference of the capillary column second virtual circle are arranged so as to form a virtual square. If so, there is no through-hole in the virtual square, and by making the capillary meander in an area within the virtual square, it is not necessary to care about the interference with any of the through-holes in terms of arrangement at all, which makes it very easy to make a design.

Further, in order to make it possible to form a more complicated flow path shape without use of a valve or the like by increasing only one more type of a plate having a different shape from the plate-type capillary column, and more easily form a flow path for a parallel, heartcutting, or a backflush, it is only necessary that a capillary column unit is provided with: the above-described plate-type capillary column; and a branching flow path board that is stacked on the plate-type capillary column, wherein the branching flow path board has: a board having a third face plate part and a fourth face plate part that face to each other; a third bottom-equipped hole that is formed so as to open in the third face plate part; a fourth bottom-equipped hole that is formed so as to open in the fourth face plate part; a fifth bottom-equipped hole that opens in any one of the third face plate part and the fourth face plate part; and a narrow tube that is formed in the board so as to connect the third bottom-equipped hole, the fourth bottom-equipped hole, and the fifth bottom-equipped hole to one another, and in the case of stacking the plate-type capillary column and the branching flow path board on each other with the second face plate part and the fourth face plate part facing to each other, the fourth bottom-equipped hole and the fifth bottom-equipped hole are arranged so as to be communicatively connected to the second bottom-equipped hole and one of the through-holes, respectively.

In order to, in the case of stacking the branching flow path board and the plate-type capillary column, make it easy to switch a communicative communication relationship between any two of the through-holes and bottom-equipped holes only by rotating any of the members, it is only necessary that in the branching flow path board, as viewed from a direction vertical to the third face plate part or the fourth face plate part, on a branching flow path board first virtual circle having the same radius as a radius of the capillary column first virtual circle, the fourth bottom-equipped hole and the fifth bottom-equipped hole are formed, and also, on the circumference of the branching flow path board first virtual circle, one or more through-holes penetrating through the third face plate part and the fourth face plate part are formed.

Specific examples of a position of the third bottom-equipped hole, which in the case of stacking the plate-type capillary column and branching flow path board having the same outer shape to form a complicated flow path, enables a method for the stacking to be simplified include one where in the branching flow path board, as viewed from the direction vertical to the third face plate part or the fourth face plate part, the third bottom-equipped hole is present at a virtual center of the branching flow path board first virtual circle.

Other arrangement examples of the third bottom-equipped hole, which in the case of forming a complicated flow path with the plate-type capillary column and the branching flow path board, facilitates a method for stacking them, or the like, include one where in the branching flow path board, as viewed from the direction vertical to the third face plate part or the fourth face plate part, the third bottom-equipped hole is present on the circumference of the branching flow path board first virtual circle.

In order to, in the case of using the plate-type capillary column and the branching flow path board to make a very complicated flow path like flow path for performing heartcutting, make it easy to configure the flow path, it is only necessary that in the branching flow path board, as viewed from the direction vertical to the third face plate part or the fourth face plate part, on a branching flow path board second virtual circle that is a circle concentric with the branching flow path board first virtual circle and has the same radius as a radius of the capillary column second virtual circle, a sixth bottom-equipped hole that is provided so as to open in the third face plate part, and a seventh bottom-equipped hole that opens in any one of the third face plate part and the fourth face plate part are provided.

In particular, specific embodiments of a capillary column unit that can adjust a length of a capillary only by preparing one type of member include a capillary column unit in which a plurality of plate-type capillary columns are stacked, wherein the respective plate-type capillary columns are stacked such that the first face plate part of one of the plate-type capillary columns is brought into contact with the first face plate part of the other plate-type capillary column, or the second face plate part of one of the plate-type capillary columns is brought into contact with the second face plate part of the other plate-type capillary column, and also the first bottom-equipped hole of one of the plate-type capillary columns is communicatively connected to the first bottom-equipped hole of the other plate-type capillary column, or the second bottom-equipped hole of one of the plate-type capillary columns is communicatively connected to the second bottom-equipped hole of the other plate-type capillary column.

In the case where a chromatograph uses the plate-type capillary column or the capillary unit, the chromatograph can be formed with space being saved, and also various types of capillary column units can be formed with a small number of part types, so that various types of conventional measuring methods can be performed.

Advantageous Effects of Invention

As described, according to the plate-type capillary column of the present invention, only by preparing one type of shape, a capillary having an arbitrary length can be configured as a whole by stacking the plate-type capillary columns with alternately reversing each of the plate-type capillary columns. Accordingly, by adjusting a length of the capillary depending on a measuring object, resolution of a chromatograph can be improved. Further, a capillary shape, length, or the like is not required to be made different between individual plate-type capillary columns, but can be limited to one type of shape, length, or the like, and therefore a working process taking time and effort, such as applying a liquid phase inside the capillaries, can also be limited to one type of process to easily reduce manufacturing cost. Also, according to the capillary column unit or gas chromatograph using such a plate-type capillary column, extensibility can be easily added, and without use of a valve or the like, a flow path having a complicated shape can be formed, so that a measuring method for heart-cutting, a backflush, or the like can be performed with use of the plate-type capillary column.

REFERENCE SIGNS LIST

Figure 1:
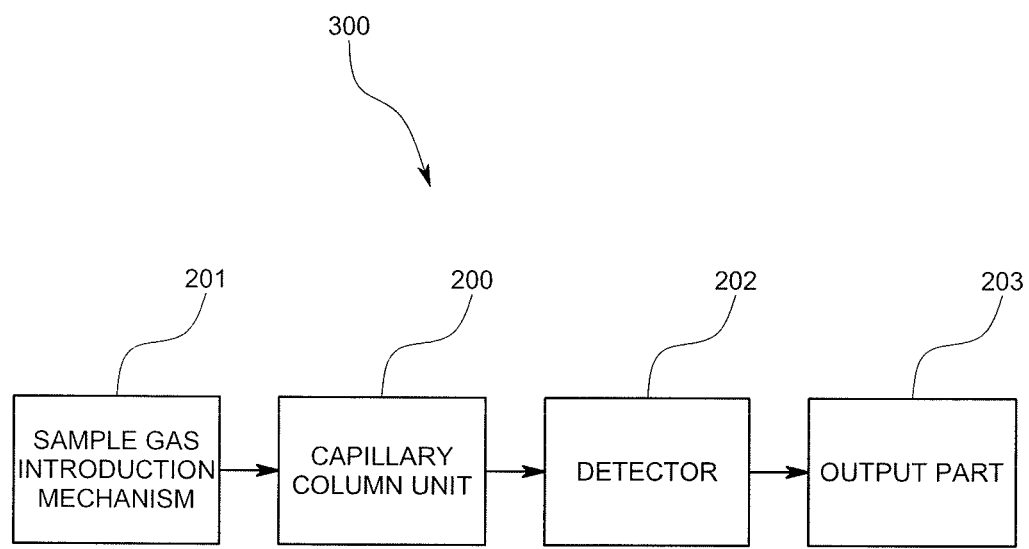
FIG. 1 is a schematic conceptual diagram illustrating a configuration of a chromatograph of the present invention.

300 Chromatograph
200 Capillary column unit
100 Plate-type capillary column
101 Branching flow path board
1 First face plate part
11 First bottom-equipped hole
2 Second face plate part
21 Second bottom-equipped hole
6 Capillary
7 Through-hole
P Plate
P1 First plate element
P2 Second plate element
C1 Capillary column first virtual circle
C2 Capillary column second virtual circle
101 Branching flow path board
CD1 Branching flow path board first virtual circle
CD2 Branching flow path board second virtual circle
3 Third face plate part
31 Third bottom-equipped hole
4 Fourth face plate part
41 Fourth bottom-equipped hole
51 Fifth bottom-equipped hole
h1 Sixth bottom-equipped hole
h2 Seventh bottom-equipped hole
8 Narrow tube
9 Through-hole
H Board

DESCRIPTION OF EMBODIMENTS

A first embodiment of the present invention is described with reference to respective drawings.

A gas chromatograph 300 of the first embodiment is one that is, as illustrated in FIG. 1, configured to include: a capillary column unit 200 formed by stacking plate-type capillary columns 100, in which a liquid phase is applied to at least part of a capillary to form a stationary phase; a sample gas introduction mechanism 201 that introduces a sample including one or more components into an internal flow path of the capillary column unit 200 together with carrier gas; and a detector 202 that is provided at an outlet of the internal flow path of the capillary column unit 200 and detects the respective components in the sample gas. Also, the gas chromatograph 300 is one that is further provided with an output part 203 that, on the basis of: a retention time that is a period of time from the introduction of the sample gas to the detection of the respective components in the sample; a retention ratio that is calculated on the basis of the retention time; a relative index; and the like, outputs what substance each of the components in the sample corresponds to.

The capillary column unit 200 is one that is configured by stacking the plurality of plate-type capillary columns 100 having the same shape as well as mutually communicatively connecting capillaries 6 respectively formed inside the plate-type capillary columns 100.

As illustrated in FIG. 2(a), each of the plate-type capillary columns 100 has a face plate part that is square-shaped, and is one that is formed in a thin plate shape as a whole and provided with: a plate P having a first face plate part 1 and a second face plate part 2 that face to each other; the capillary 6 that is formed inside the plate P; and bottom-equipped holes 11 and 21 and through-holes 7 that are made in a direction vertical to the respective face plate parts 1 and 2 of the plate P. That is, the capillary 6 is a flow path formed in the plate P, and formed not to open to the outside except at the respective connected bottom-equipped holes 11 and 12. Accordingly, the capillary 6 is formed not to come into contact with outer air except at one end part and the other end part that are respectively connected to the bottom-equipped holes 11 and 21, and for example, adapted to keep a lateral face part sealed without placing a lid or the like with another member.

The place P is one that is, as illustrated in FIG. 2(b) formed by attaching two thin plates on each other, and configured to include: a first plate element P1 formed with a groove on a front surface thereof and a second plate element P2 that is attached so as to cover the front surface of the first plate element P1.

The first plate element P1 is, for example, a thin quartz glass plate, and on the front surface thereof, the minute groove is formed by a processing method such as etching. In the present embodiment, as viewed from the direction vertical to the front surface, the groove is formed in a spiral shape that expands from the central point of the square to one of the four corners of the square. Note that, in the view, the number of turns of the spiral is displayed as approximately three for simplicity; however, the number of turns may be increased by forming the groove more minutely. Also, by attaching the second plate element P2 that is quartz glass having the same shape as that of the first plate element P1 on the first plate element P1 such that the respective plate elements P1 and P2 overlap each other, an opening side of the groove is blocked to form the plate-type capillary column 100 having the capillary 6 inside.

Figure 2:
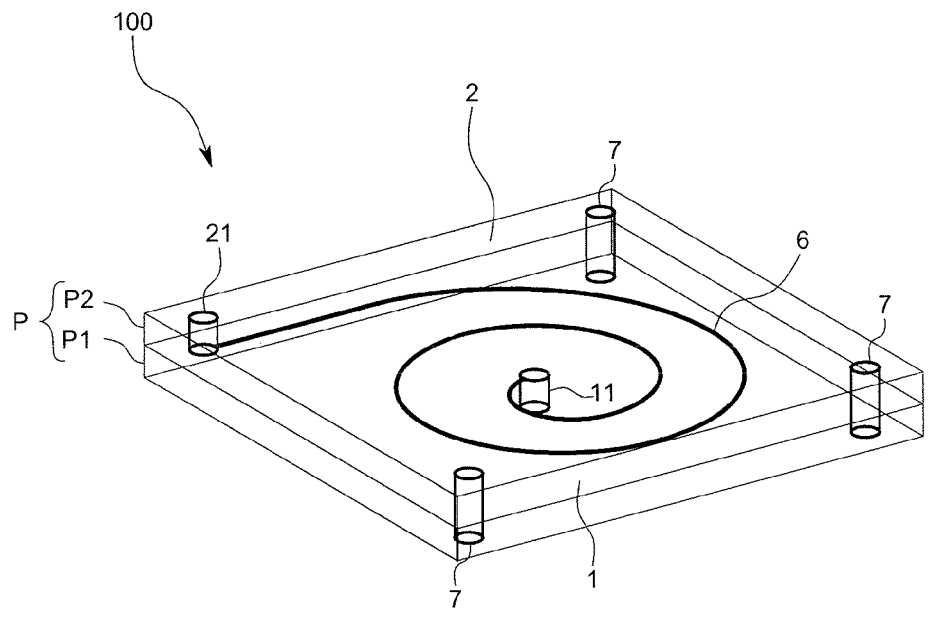
FIG. 2 includes a schematic perspective view and schematic exploded perspective view illustrating a plate-type capillary column in an embodiment of the present invention.
Figure 2:
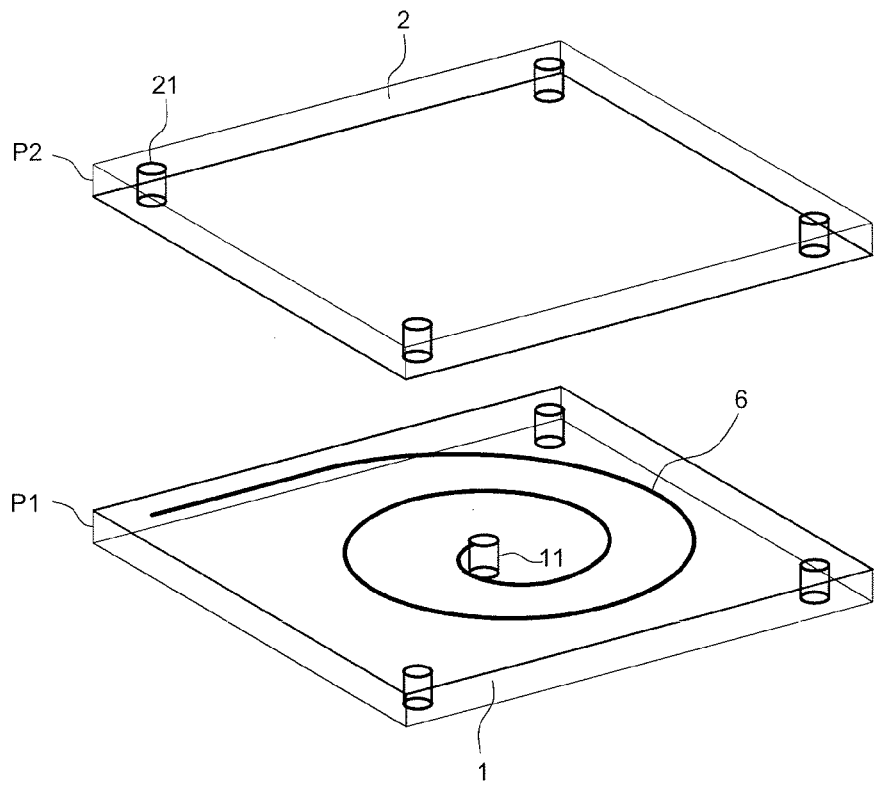
Figure 3:
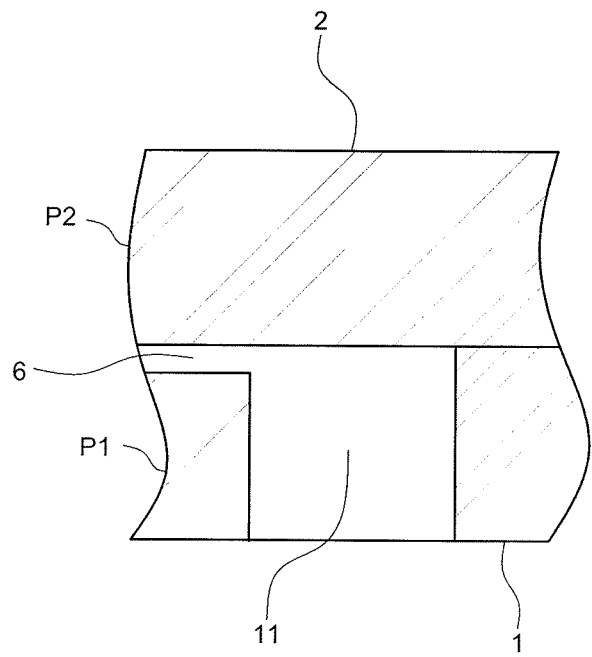
FIG. 3 is a schematic cross-sectional view illustrating structure near a first bottom-equipped hole and a second bottom-equipped hole of the plate-type capillary column.
Figure 3:
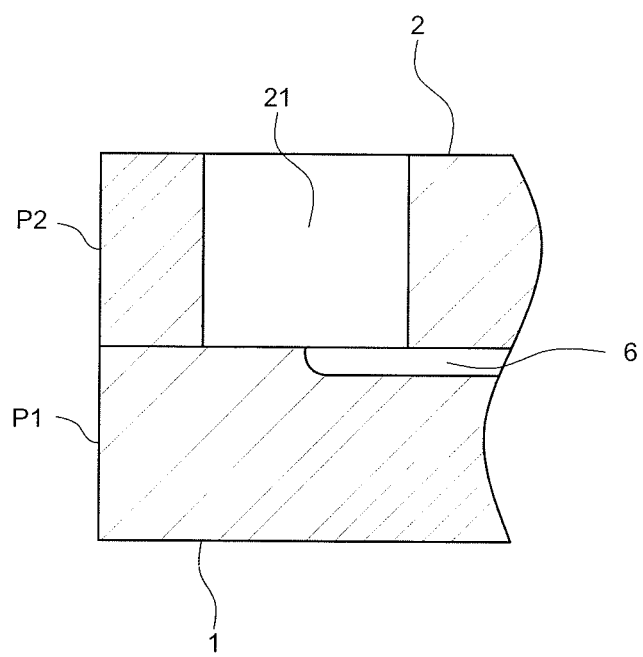

Further, in FIG. 2(a), in the first face plate part 1 corresponding to a lower surface (back surface of the first plate element P1) of the plate-type capillary column 100, at the center thereof, the first bottom-equipped hole 11 is formed so as to be connected to the one end part of the capillary 6. The first bottom-equipped hole 11 is one that is, as illustrated in FIG. 3(a), formed so as to penetrate through only the first plate element P1, and by not forming a hole at the center of the second plate element P2, adapted to be a bottom-equipped hole with the respective plate elements P being attached on each other. Also, as illustrated in FIG. 2, the first bottom-equipped hole 11 is formed such that the one end part on the center side of the capillary 6 formed so as to draw a spiral intersects with a lateral face of the first bottom equipped hole 11. In addition, at the four corners of the first plate element P1, parts of the through-holes 7 penetrating through in a thickness direction are formed so as to, by connecting central axes thereof, form a virtual square. That is, the four holes in total are formed in the first plate element P1 so as to penetrate through the face plate part.

On the other hand, a back surface of the second plate element P2 is attached on a front surface of the first plate element P1, and also a front surface of the second plate element 2 forms an upper surface of the plate-type capillary column 100. Also, as illustrated in FIG. 2, at three of the four corners of the second plate element P2, parts of the through-holes 7 that have the same arrangement and diameter as those in the first plate element P1 and penetrate through in the thickness direction are formed. Further, in the view of FIG. 2, one hole formed at the upper left is arranged so as to be connected to an outer end that is the other end part of the spiral capillary 6 as illustrated in FIG. 3(b). In the first plate element P1, as illustrated in FIG. 2, a hole is not formed at the upper left corner, and therefore the present embodiment is adapted to form the second bottom-equipped hole 21 with attaching the respective plate elements P1 and P2 on each other. In addition, the parts of the other through-holes 7 are communicatively connected to the parts of the through-holes 7 of the first plate element P1, and thereby the present embodiment is adapted to form the through-holes 7 of the plate-type capillary column 100.

Accordingly, in a state of the plate-type capillary column 100 combining the first plate element P1 and the second plate element P2 with each other, as illustrated in FIG. 2, as viewed from the direction vertical to the first face plate part 1 or the second face plate part 2, at the center of the first face plate part 1, the first bottom-equipped hole 11 is formed, and on a capillary column first virtual circle C1 that is present around a central axis of the first bottom-equipped hole 11 and has, as a radius, a straight line connecting to a central axis of the second bottom-equipped hole 21, the three through-holes 7 are formed. Alternatively, from another perspective, the second bottom-equipped hole 21 and through-holes 7 are arranged with respect to the face plate parts so as to be rotational symmetric around the central axis of the first bottom-equipped hole 11. More specifically, the second bottom-equipped hole 21 and the respective through-holes 7 are arranged so as to be 90-degree rotational symmetric around the central axis of the first bottom-equipped hole 11, which corresponds to a virtual center of the plate-type capillary column 100. Accordingly, in the case of rotating one plate-type capillary column 100 by 90 degrees with respect to the other plate-type capillary column 100, positions of the second bottom-equipped hole 21 and the respective through-holes 7 of one of the plate-type capillary columns 100 coincide with those of the other one 100. Note that, in the present embodiment, around the virtual center, the second bottom-equipped hole 21 and the respective through-holes 7 are arranged so as to be rotational symmetric; however, in some cases, it is not necessary to arrange them rotational symmetrically. In short, it is only necessary that the second bottom-equipped hole 21 and the respective through-holes 7 are arranged on the capillary column first virtual circle C1. If so, by stacking the plate-type capillary columns 100 and rotating one of them around the virtual center, holes desired to be connected to each other can be connected to each other with use of the second bottom-equipped holes 21 and the through-holes 7, and a desired flow path can be easily formed.

An example of use of the capillary column unit 200 in which only the plate-type capillary columns 100 each configured as above are stacked in the thickness direction is described with reference to drawings such as FIG. 4. Note that, in the following description, for convenience of description, even in the case of the plate-type capillary columns 100 having the same shape, to make it easier to distinguish them from each other, in the views of the drawings, the plate-type capillary column 100 located on the upper side, and that located on the lower side are further affixed with t and b, respectively. However, even in the case where the added symbols are different, the respective plate-type capillary columns 100t and 100b are completely the same in shape.

Figure 4:
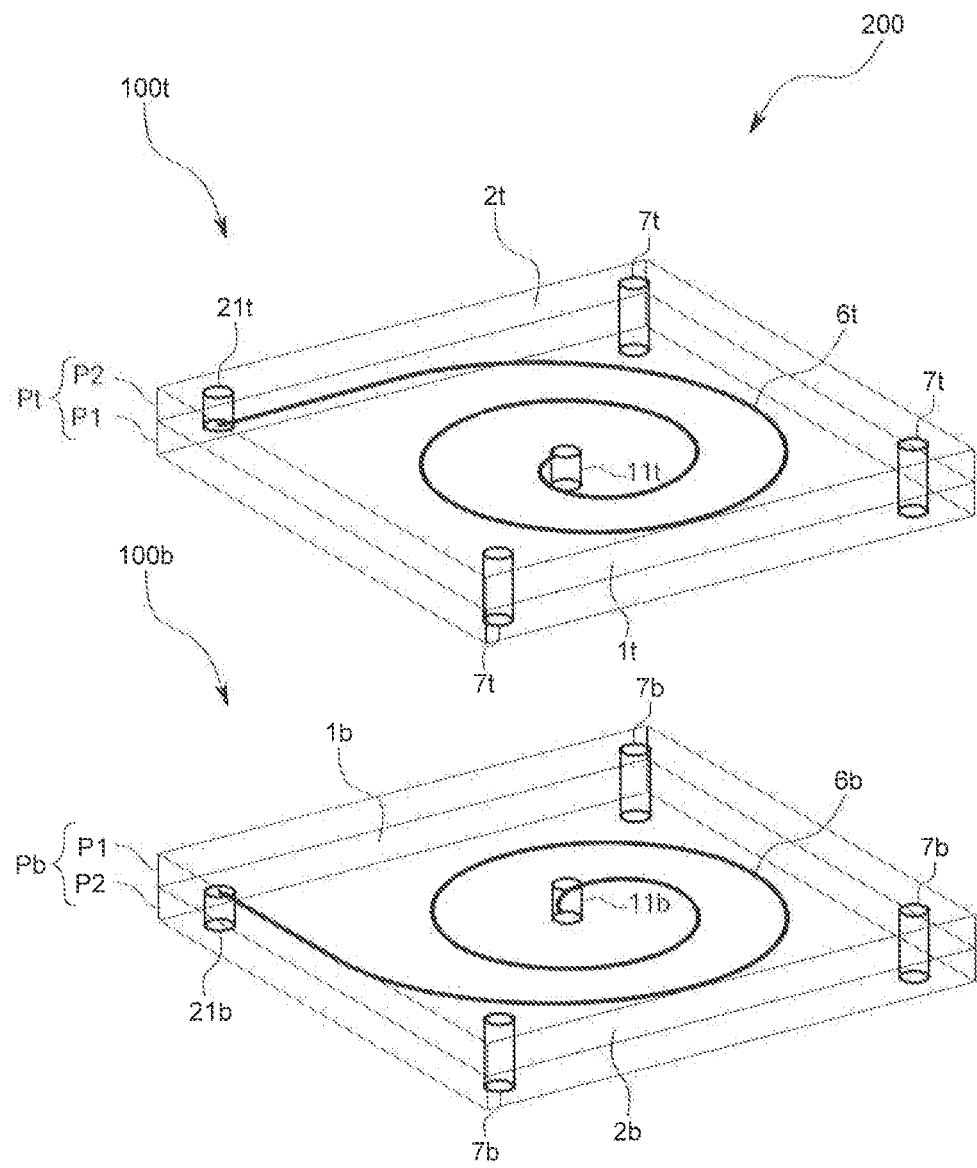
FIG. 4 is a schematic exploded perspective view of a capillary column unit in a first embodiment.
Figure 5:
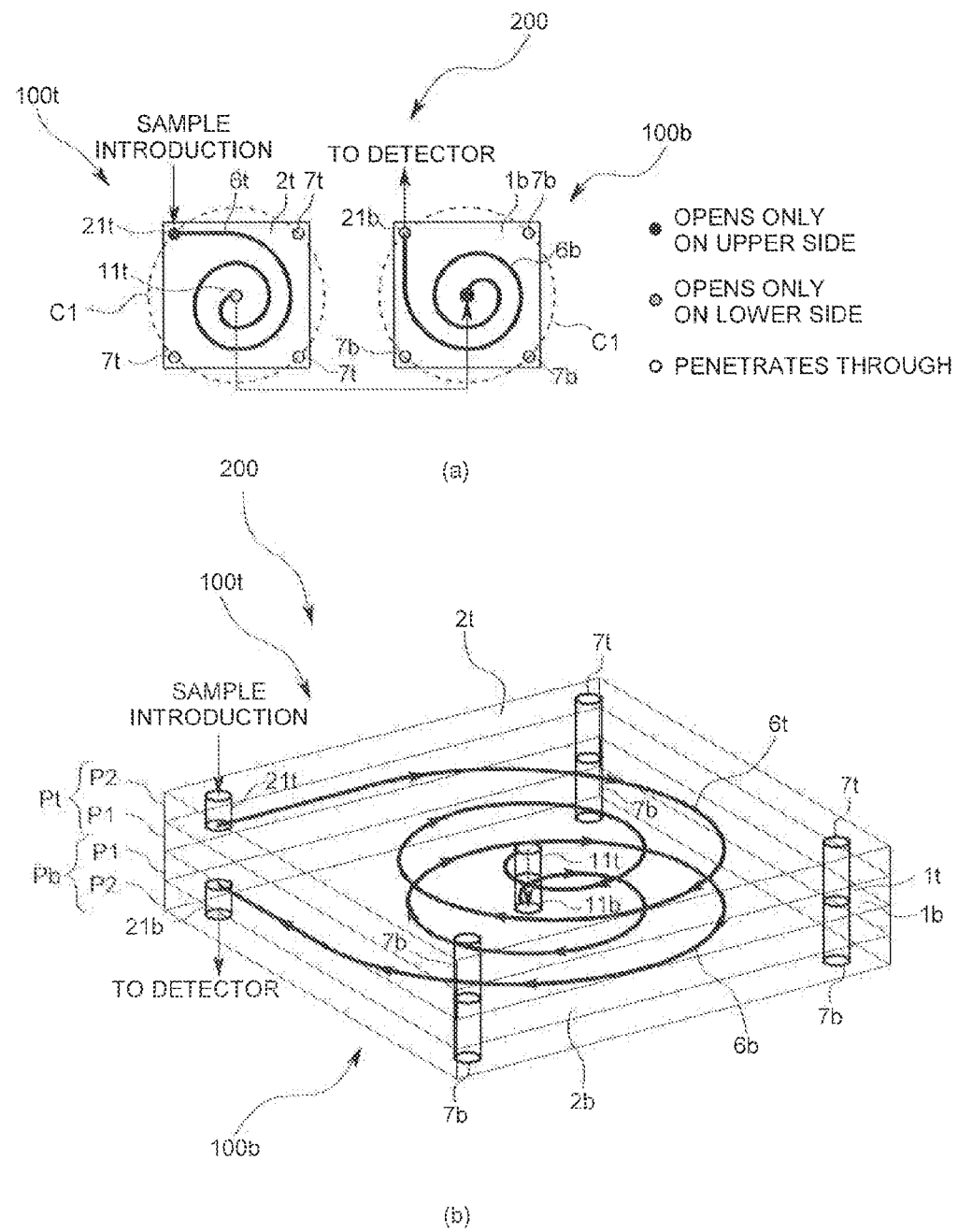
FIG. 5 includes a flow path diagram and schematic perspective view of the capillary column unit in the first embodiment.

The description is provided with, as illustrated in FIG. 4, as in the lower side plate-type capillary column 100b, a state where a first face plate 1b and a second face plate 2b are arranged on the upper and lower sides respectively, and a second bottom-equipped hole 21b is arranged at the upper left being regarded as a reference state. With respect to the lower side plate-type capillary columns 100b, the upper side plate-type capillary columns 100t is set up such that a relative location between respective face plate parts 1t and 2t is reversed, i.e., the first face plate part it and the second face plate side 2t are arranged on the lower and upper sides, respectively, and the upper side plate-type capillary column 100t is rotated around a first bottom-equipped hole 11t such that a second bottom-equipped hole 21t is located on an upper left side as in the lower side plate-type capillary column 100b. By stacking the respective plate-type capillary columns 100t and 100b such that sides of a plate Pt and sides of a plate Pb coincide with each other, the capillary column unit 200 as in a flow path conceptual diagram illustrated in FIG. 5(a) and in a perspective view illustrated in FIG. 5(b) can be formed.

A gas flow in the case of using such a capillary column unit 200 to configure the gas chromatograph 300 is described. When the sample is introduced together with the carrier gas by the sample gas introduction mechanism 201 into the second bottom-equipped hole 21t of the upper side plate-type capillary column 100t, the sample together with the carrier gas passes through a capillary 6t inside the upper side plate-type capillary column 100t to reach the first bottom-equipped hole 11t. Then, the gas containing the sample proceeds to a first bottom-equipped hole 11b of the communicatively connected lower side plate-type capillary column 100b, and passes through a capillary 6b of the lower side plate-type capillary column 100b to reach the second bottom-equipped hole 21b. Then, the sample-containing gas having exited from the second bottom-equipped hole 21b is detected by the detector 202.

As described, by using the capillary unit 200 of the first embodiment, the capillary 6 is formed inside the plate P, and also the first and second bottom-equipped holes 11 and 21 connected to the end parts of the capillary 6 respectively separately opens in the first and second face plate parts 1 and 2 that are surfaces on sides opposite to each other, so that by stacking the plate-type capillary columns 100 in the thickness direction so as to come into contact with each other on the same surfaces, the capillaries 6 can be connected to adjust a total length. In other words, the first and second bottom-equipped holes 11 and 12 provided at the end parts of the capillary 6 are adapted to open in the mutually different face plate parts, and therefore only by stacking the plate-type capillary columns 100 with alternately reversing a relative location between the face plate parts of each of the plate-type capillary columns 100, a length of a capillary 6 as a whole can be extended. Accordingly, even without use of two types of plate-type capillary columns respectively having different shapes as in the conventional case, only by manufacturing the one type of plate-type capillary column 100, the capillary 6 having an arbitrary length as a whole can be easily configured. Accordingly, depending on a measuring object, the length of the capillary 6 can be appropriately set, and therefore resolution as the chromatograph 300 can be easily increased.

Next, a capillary column unit 200 and chromatograph 300 of a second embodiment are described. Note that, in the following description, it is assumed that as a plate-type capillary column 100, the same one described in the above first embodiment is used. Also, corresponding members are affixed with the same symbols.

Figure 6:
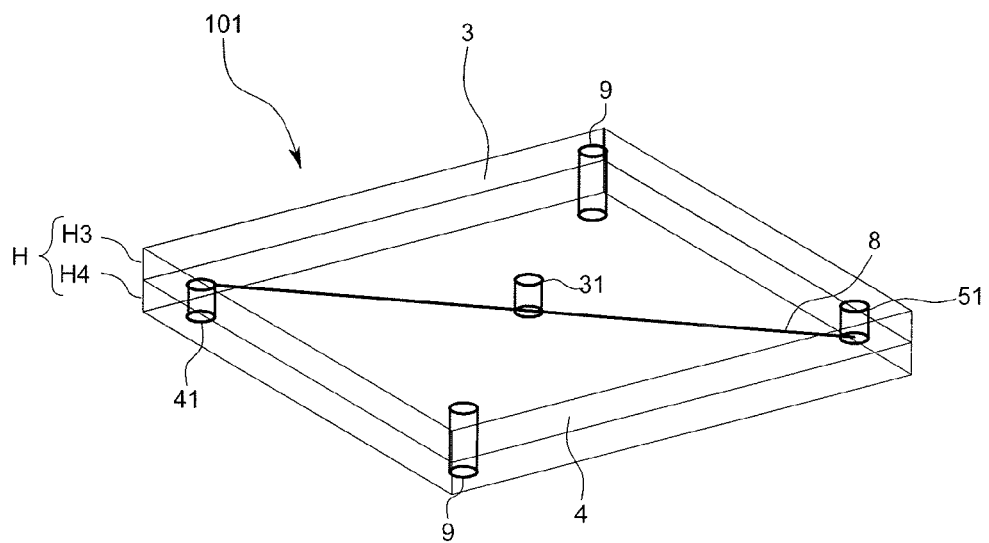
FIG. 6 includes a flow path diagram and schematic perspective view of the capillary column unit in the first embodiment.
Figure 6:
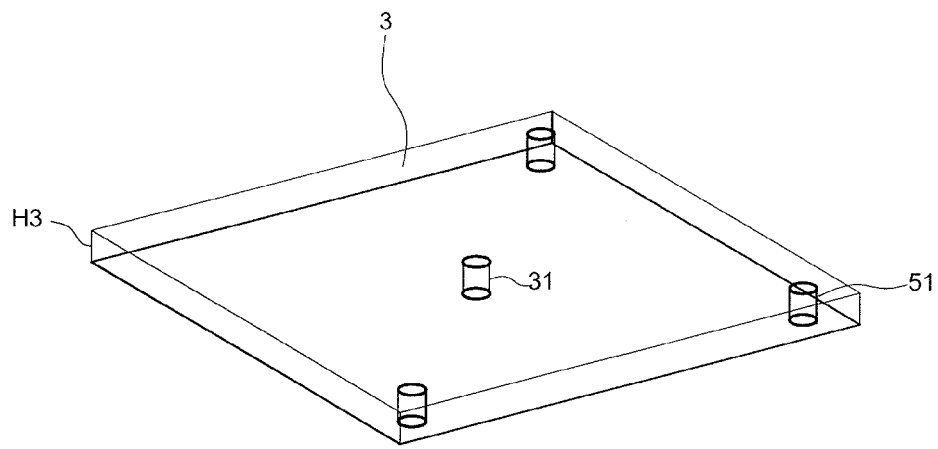
Figure 6:
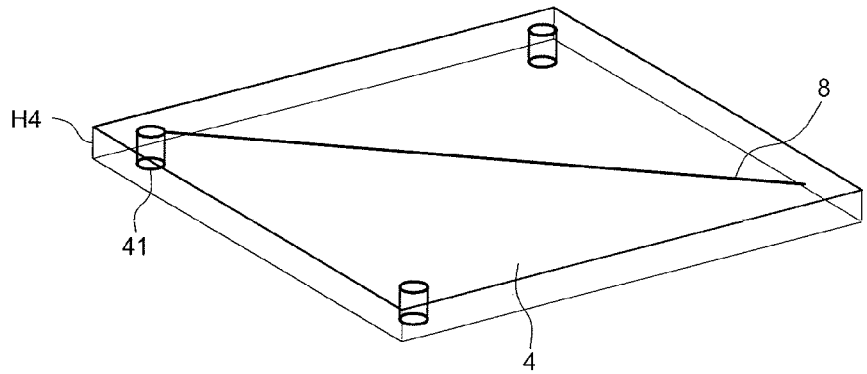

The capillary column unit 200 of the second embodiment is one that is provided with the plate-type capillary columns 100 described in the first embodiment and a branching flow path board 101 illustrated in FIG. 6.

The branching flow path board 101 is, as illustrated in FIG. 6(a), formed with use of a plate P having the same shape as that of the plate-type capillary-column 100, and at positions where in the plate-type capillary column 100, the respective bottom-equipped holes and through-holes 7 are formed, bottom-equipped holes and through-holes are similarly formed. In the following, to make easier to distinguish the respective members from each other, for convenience of description, the plate P and the capillary 6 in the plate-type capillary column 100 are, in the branching flow path board 101, described as a board H and a narrow tube 8, respectively.

The branching flow path board 101 is one that, as illustrated in FIG. 6(a), has: the board H having a third face plate part 3 and a fourth face plate part 4 that face to each other; a third bottom-equipped hole 31 that is formed so as to open in the third face plate part 3; a fourth bottom-equipped hole 41 that is formed so as to open in the fourth face plate part 4; a fifth bottom-equipped hole 51 that opens in any one of the third face plate part 3 and the fourth face plate part 4; and the narrow tube 8 that is formed in the board H so as to connect the third bottom-equipped hole 31, the fourth bottom-equipped hole 41, and the fifth bottom-equipped hole 51 to one another.

The branching flow path board 101 is also formed in a thin plate shape having a face plate part that is square shaped, and as illustrated in FIG. 6(b), as with the plate-type capillary column 100, configured to include two board elements H3 and H4 into which the branching flow path board 101 is divided in a thickness direction. Also, by forming a groove on a front surface of one H3 of the board elements, and attaching the other board element H4 on the board element H3 to lid the groove with mutually overlapping both of the board elements H3 and H4, the narrow tube 8 for flowing sample gas and carrier gas inside is formed. Note that the narrow tube 8 is not applied with a liquid phase inside; adapted such that a measurement sample flows at a speed equal to that at which the measurement sample flows in normal space; and does not largely influence measured values such as a retention time. That is, the present embodiment is configured such that the measured values such as the retention time measured at the time of use as the chromatograph 300 are substantially determined by the capillaries 6 of the plate-type capillary columns 100.

To describe the respective holes provided in the branching flow path board 101, the third bottom-equipped hole 31 opening in the third face plate part 3 corresponding to an upper surface in FIG. 6(a) is formed so as to pass through the center of the board H. Also, at the four corners of the board H, the fourth bottom-equipped hole 41, fifth bottom-equipped hole 51, and through-holes 7 are formed so as to form a square shape. In the second embodiment, the fourth bottom-equipped hole 41 and the fifth bottom-equipped hole 51 are diagonally arranged, and also the fifth bottom-equipped hole 51 is adapted to open only in the third face plate part 3. Further, the narrow tube 8 connecting the respective bottom-equipped holes is formed on one straight line so as to form a diagonal of the board H.

From another perspective, as viewed from a direction vertical to the third board part 3 or the fourth board part 4, on a branching flow path board first virtual circle CD1 that, as a virtual center, sets a central axis of the third bottom-equipped hole 31 opening in the third board part 3 corresponding to the upper surface in FIG. 6 and has the same radius as that of the capillary column first virtual circle C1, the fourth bottom-equipped hole 41 and the fifth bottom-equipped hole 51 are formed, and also, on the branching flow path board first virtual circle CD1, the two through-holes that penetrate through the third face plate part 3 and the fourth face plate part 4 are provided. The two through-holes 9 are arranged to form a diagonal different from the diagonal formed by the fourth bottom-equipped hole 41 and the fifth bottom-equipped hole 51. More strictly, along a circumference of the branching flow path board first virtual circle CD1, the forth bottom-equipped hole 41, through-hole 9, fifth bottom-equipped hole 51, and through-hole 9 are arranged in this order so as to be 90-degree rotational symmetric around the third bottom-equipped hole 31.

In the following, the capillary column unit 200 using such a branching flow path board 101 is described for each of various types of measuring methods.

<Parallel>

Figure 7:
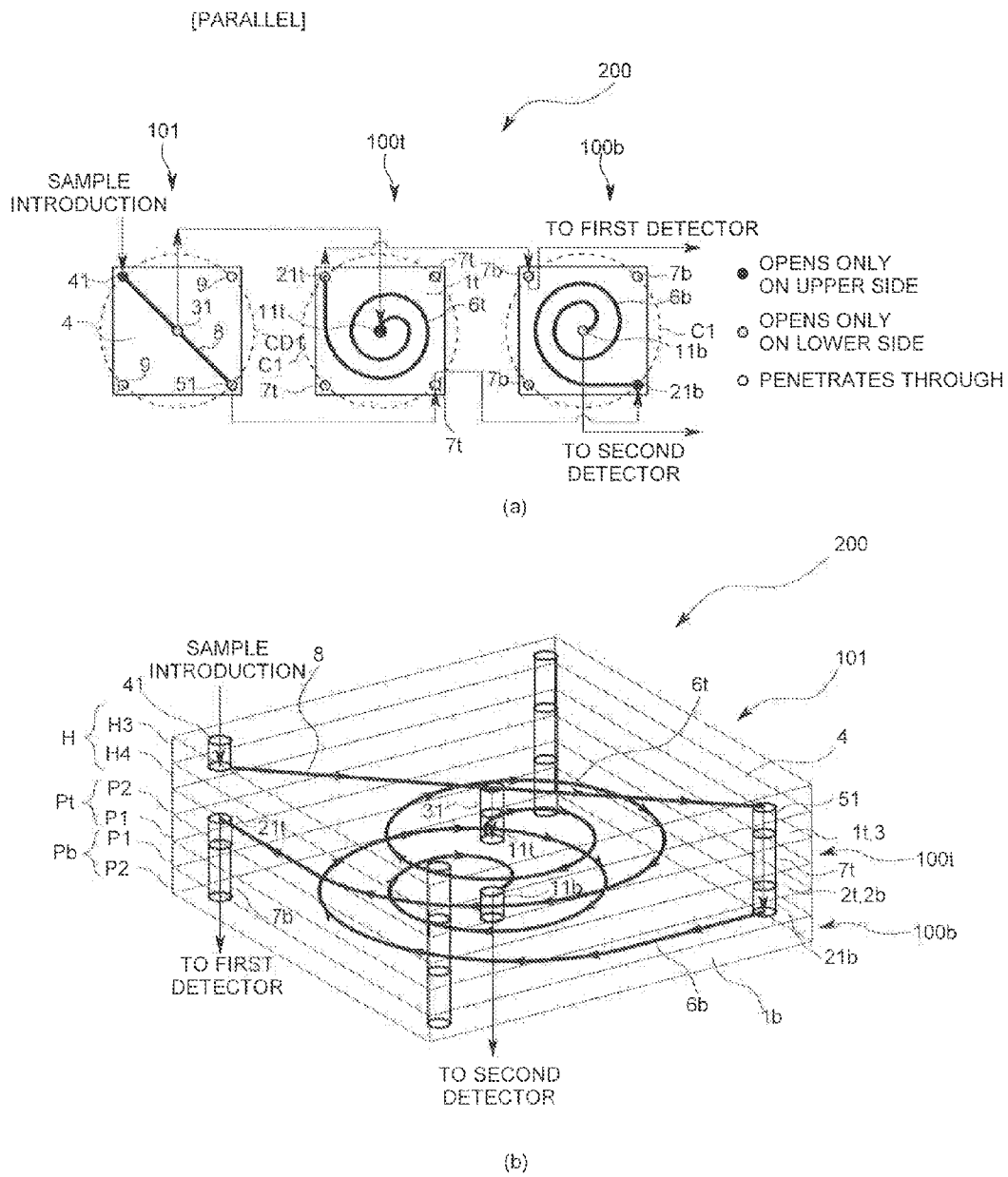
FIG. 7 includes a schematic perspective view and schematic exploded perspective view illustrating structure of a branching flow path board used for a capillary column unit in a second embodiment.

A configuration of a capillary column unit 200 illustrated in FIG. 7 is one intended to realize a parallel measuring method that is adapted such that a sample introduced from one sample introduction port passes through two parallel provided flow paths separately, and then the separated samples are respectively led out to different detectors 202. For example, by making the types of stationary phases in the respective flow path different, components in the sample can be more easily identified.

The capillary column unit 200 used for the parallel measuring method is configured with use of one branching flow path board 101 and two plate-type capillary columns 100, in which the branching flow path board 101 is provided in the uppermost layer, and the two plate-type capillary column 100 are stacked on the lower side of the branching flow path board 101.

In FIG. 7, the branching flow path board 101 is arranged such that the fourth face plate part 4 is located on the upper side, and adapted to introduce sample gas from the fourth bottom-equipped hole 31 formed in illustrated in FIGS. 7(a) and 7(b), the third bottom-equipped hole 31 formed in the central part of the third face plate part 3 of the branching flow path board 101 is adapted to be communicatively connected to the first bottom-equipped hole 11$t$ of the plate-type capillary column 100$t$ present in the middle layer. Further, the fifth bottom-equipped hole 51 formed at a corner of the third face plate part 3 of the branching flow path board 101 is adapted to be communicatively connected to a through-hole 7$t$ of the plate-type capillary column 100$t$ present in the middle layer. The through-hole 7$t$ of the plate-type capillary column 100$t$ presents in the middle layer, which is communicatively connected with the fifth bottom-equipped hole 51, is further communicatively connected to the second bottom-equipped hole 21$b$ formed at a corner of the second face plate part 2$b$ of the plate-type capillary column 100$b$ present in the lowermost layer.

A flow of the sample gas in the capillary column unit 200 configured as described is described.

First, the sample gas introduced from the fourth bottom-equipped hole 41 of the branching flow path board 101 passes through the narrow tube 8, and branches into sample gas flowing from the third bottom-equipped hole 31 present in the central part to the middle layer, and sample gas flowing from the fifth bottom-equipped hole 51 present at the corner to the lowermost layer.

The sample gas having entered the middle layer from the third bottom-equipped hole 31 passes through the capillary 6$t$ of the middle layer plate-type capillary column 100$t$ from the central end to the outer end, and flows from the second bottom-equipped hole 21$t$ at the outer end to a first detector 202 through the through-hole 7$b$ of the plate-type capillary column 100$b$ in the lowermost layer.

On the other hand, the sample gas having flowed from the fifth bottom-equipped hole 51 of the branching flow path board 101 to the lowermost layer passes through the capillary 6$b$ of the lowermost layer plate-type capillary column 100$b$ from the outer end to the central end, and flows from the first bottom-equipped hole 11$b$ to a second detector 202.

As described, the combination of the plate-type capillary columns 100 and the branching flow path board 101 enables the sample gas to be simultaneously flowed through the separated flow paths, and therefore, for example, flow paths respectively having different stationary phase properties can be used to perform chromatographic analysis in parallel.

<Backflush>

Next, a configuration of a capillary column unit 200 that can perform a backflush for discharging remaining components accumulated in the capillary 6 is described. Examples of the configuration for the backflush include one where, as illustrated in FIG. 8, from the upper layer, the plate-type capillary column 100t of which the second face plate part 2t is located on the upper side, the branching flow path board 101 of which the third face plate part 3b is located on the upper side, and the plate-type capillary column 100b of which the second face plate part 2b is located on the upper side are arranged in this order.

Also, between the upper layer plate-type capillary column 100t and the branching flow path board 101, the first bottom-equipped hole 11t and the third bottom-equipped hole 31 are communicatively connected to each other, and a through-hole 7t and the fifth bottom-equipped hole 51 are also communicatively connected to each other. Between the branching flow path board 101 and the lowermost layer plate-type capillary column 100b, the third bottom-equipped hole 31 and the second bottom-equipped hole 21b are communicatively connected to each other.

Further, the capillary column unit 200 is adapted to introduce sample gas from the second bottom-equipped hole 21t of the upper layer plate-type capillary column 100t, and also from the through-hole 7t communicatively connected to the fifth bottom-equipped hole 51 of the branching flow path, introduce pressure adjustable gas of which pressure is adjustable.

Figure 8:
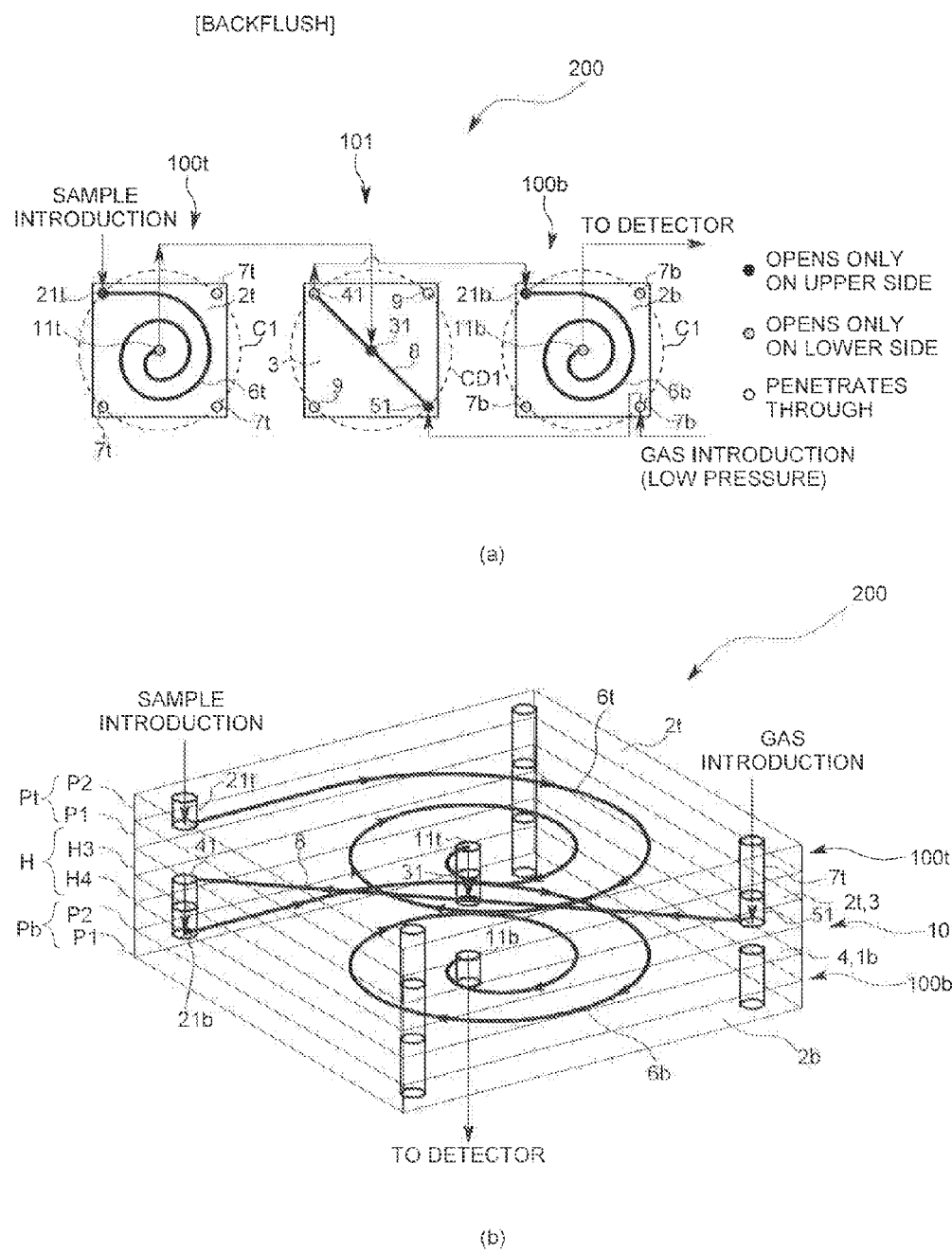
FIG. 8 includes a flow path diagram and schematic perspective view of a capillary column unit having a flow path configuration for a backflush at the time of measurement.

At the time of normal measurement, the pressure of the pressure adjustable gas is set smaller than a pressure of the sample gas, and therefore as illustrated in FIG. 8, the sample gas having passed through the capillary 6t of the upper layer plate-type capillary column 100t passes through the narrow tube 8 from the third bottom-equipped hole 31 of the branching flow path only toward the fourth bottom-equipped hole 41 side, and flows into the lowermost layer plate-type capillary column 100b. Then, the sample gas reaches a detector 202 from the first bottom-equipped hole 11b of the lowermost layer plate-type capillary column 100b.

Figure 9:
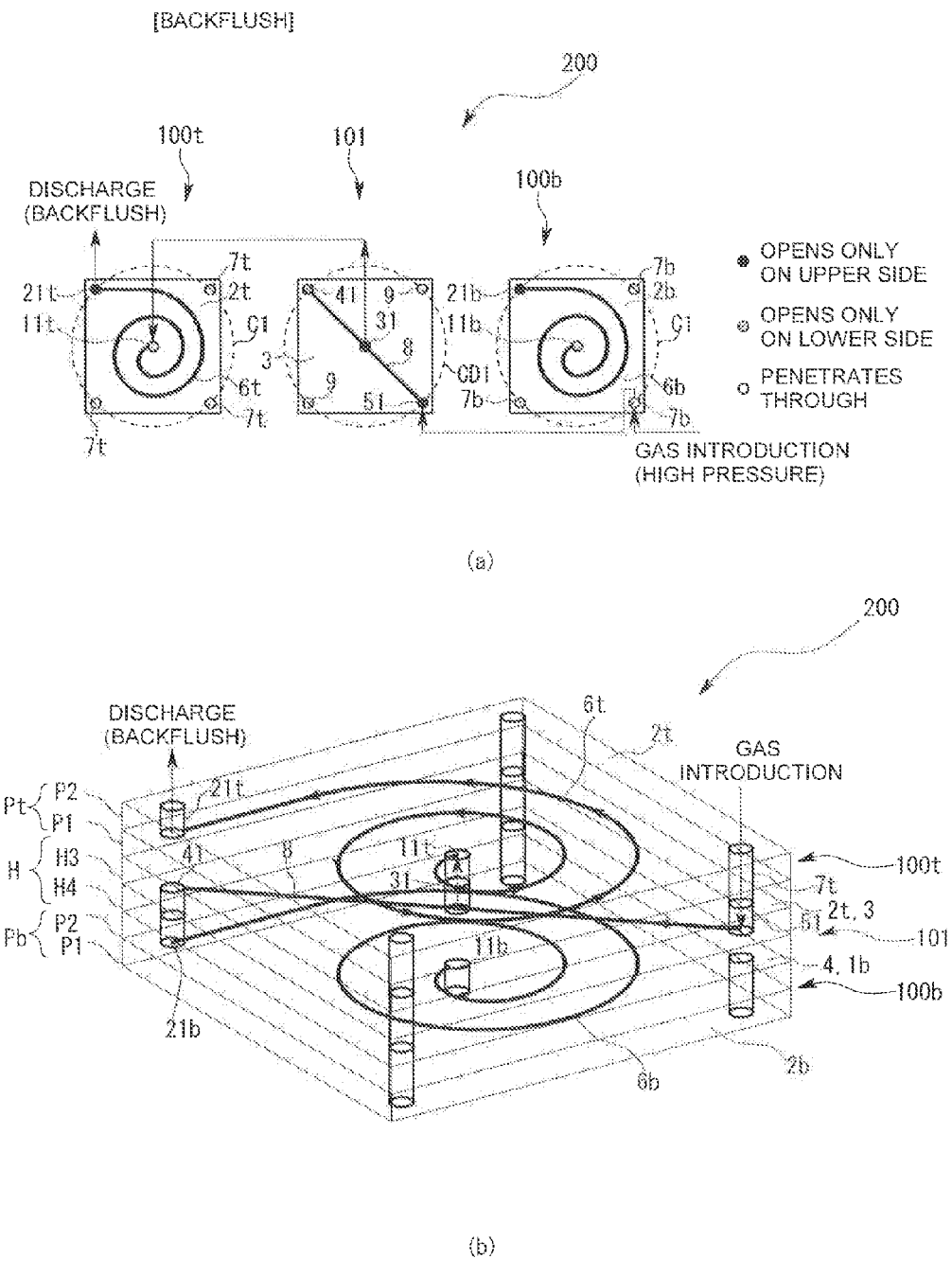
FIG. 9 includes a flow path diagram and schematic perspective view of the capillary column unit having the flow path configuration for a backflush at the time of discharge.

On the other hand, in the case of setting the pressure of the pressure adjustable gas to high pressure, the sample gas never reaches the detector 202, and as illustrated in FIG. 9, the pressure adjustable gas flows from the fifth bottom-equipped hole 51 of the branching flow path board 101 to the third bottom-equipped hole 31, and flows back in the upper layer plate-type capillary column 100t. For this reason, residues and the like accumulated in the upper layer plate-type capillary column 100t can be discharged from the second bottom-equipped hole 21t serving as the sample gas introduction port.

<Heartcutting>

Finally, described is a configuration of a capillary column unit 200 for heartcutting, which can select whether to perform analysis at the time when a first plate-type capillary column 100t is passed through, or perform analysis after the first plate-type capillary column 100t had been passed through, another plate-type capillary column 100b has been further passed through. In other words, the capillary column unit 200 for heartcutting is one that is configured to be able to change a length of a capillary 6 as a whole without reconfiguring the capillary column unit 200 itself at the time of measurement.

In the capillary column unit 200 for heartcutting, a configuration of the branching flow path board 101 is made different from that in the case of the parallel or the backflush. More specifically, in the branching flow path board 101, except for the third bottom-equipped hole 31 in the third face plate part 3, bottom-equipped holes opening in the fourth face plate part 4 are formed at the four corners of the fourth face plate part 4. That is, an opening direction of the fifth bottom-equipped hole 51 is changed from being toward the third face plate part 3 to being toward the forth face plate part 4, and also the two through holes 7 are changed to bottom-equipped first and second connecting holes 91 and 92 opening in the fourth face plate part 4. Further, the narrow tube 8 extending in a direction of the diagonal of the board H, which connects the third bottom-equipped hole 31, fourth bottom-equipped hole 41, and fifth bottom-equipped hole 51, are formed in a Z-shape, and extends so as to connect the third bottom-equipped hole 31 and the first connecting hole 91 to each other, and connect the fifth bottom-equipped hole 51 and the second connecting hole 92 to each other.

Figure 10:
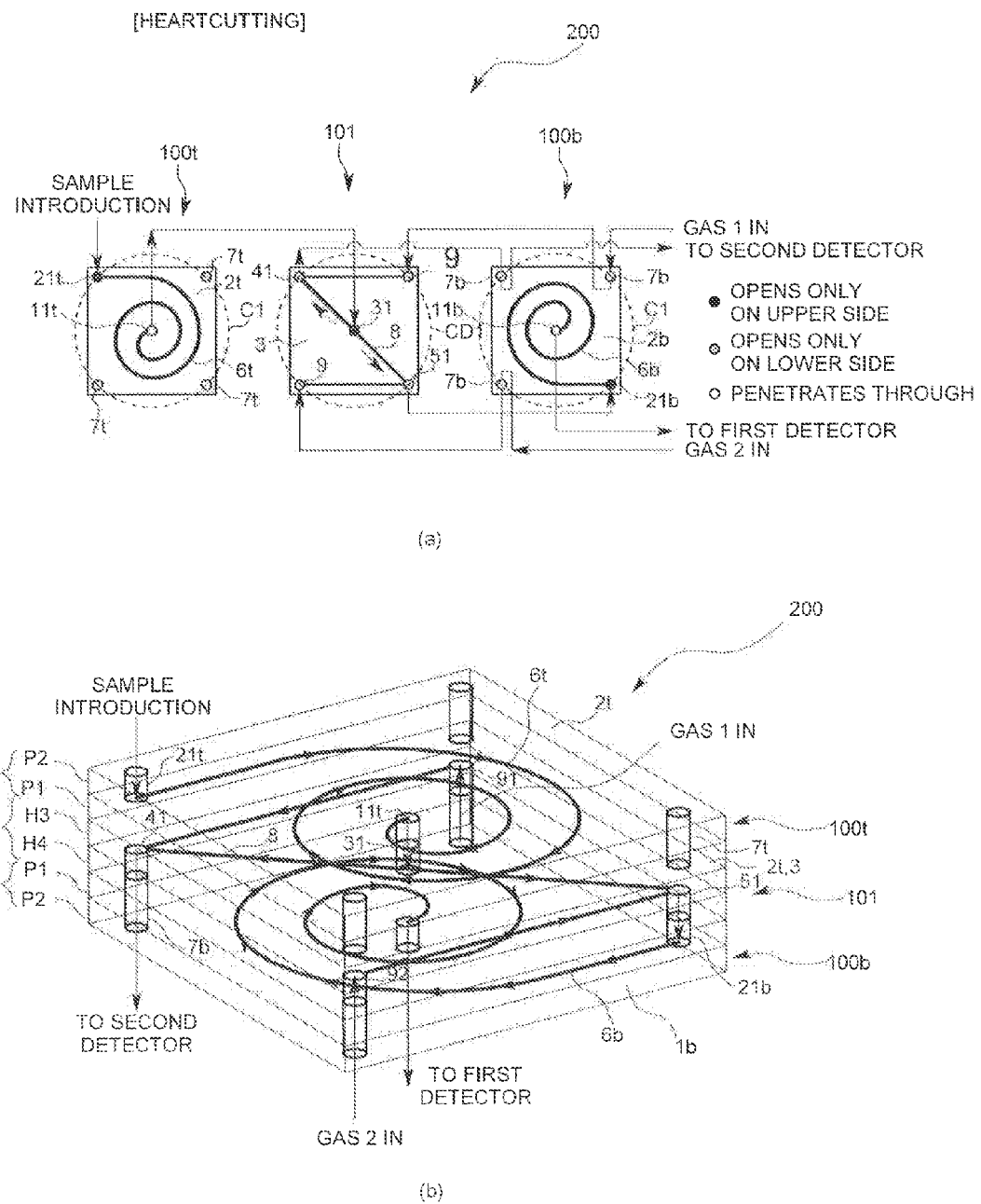
FIG. 10 includes a flow path diagram and schematic perspective view of a capillary column unit having a flow path configuration for heartcutting.

The capillary column unit 200 uses such a branching flow path board 101, and is, as illustrated in FIG. 10, from the upper layer, provided side by side with: the plate-type capillary column 100t of which the first face plate part 1t is located on the lower side; the branching flow path board 101; and the plate-type capillary column 100b of which the first face plate part 1b is located on the lower side in this order.

The upper layer plate-type capillary column 100t is, as illustrated in FIG. 10(a), adapted to arrange the first face plate part 1t on the lower side, and also communicatively connect the first bottom-equipped hole 11t and the third bottom-equipped hole 31 of the branching flow path board 101. Further, the branching flow path board 101 is adapted to communicatively connect the fourth bottom-equipped hole 41 and a through-hole 7b of the lowermost layer plate-type capillary column 100b to each other, and also communicatively connect the fifth bottom-equipped hole 51 and the second bottom-equipped hole 21b of the lowermost layer plate-type capillary column 100b to each other.

Still further, the capillary column unit 200 is configured to introduce sample gas from the second bottom-equipped hole 21t of the upper layer plate-type capillary column 100t, and also configured to be able to introduce first and second pressure adjustable gases into, among the through-holes 7b of the lowermost layer plate-type capillary column 100b, ones communicatively connected to the first and second connecting holes 91 and 92 of the branching flow path board 101, respectively.

To describe a gas flow, the sample gas introduced into the upper layer plate-type capillary column 100t flows from the first bottom-equipped hole 11t to the third bottom-equipped hole 31 of the branching flow path board 101, and enters the narrow tube 8. In the case where pressures of the first and second pressure adjustable gases are low, the sample gas flows from the third bottom-equipped hole 31 to both of the fourth bottom-equipped hole 41 and the fifth bottom-equipped hole 51 half and half, and the gas having passed through the fourth bottom-equipped hole 4311 reaches a second detector 202, whereas sample gas having passed through the fifth bottom-equipped hole 51 flows inside the lowermost layer plate-type capillary column 100b, and reaches a first detector 202 from the first bottom-equipped hole 11b. That is, in this case, in the second detector 202, component analysis of the sample gas having passed through the one capillary 6 is performed, whereas in the first detector 202, component analysis of the sample gas having passed through the two capillaries 6 is performed.

In the case where only the pressure of the first pressure adjustable gas is high, the sample gas does not flow into the fourth bottom-equipped hole 41, and therefore after the sample gas has passed through the fifth bottom-equipped hole 51 and also through the two capillaries 6, only the sample gas reaching the first detector 202 can be subjected to component analysis. On the other hand, in the case where only the pressure of the second pressure adjustable gas is high, the sample gas does not flow into the fifth bottom-equipped hole 51, and therefore after the sample gas has passed through the fourth bottom-equipped hole 41 and also through only the one capillary 6, only the sample gas reaching the second detector 202 can be subjected to the component analysis. As described, only by adjusting the pressures of the first and second pressure adjustable gases, an analysis mode for the sample gas can be appropriately changed. Any of such flow path configurations can be taken, and therefore by adjusting the pressures of the respective pressure adjustable gases during measurement, some component contained in the sample gas can be passed through only the one capillary 6, and another component can be passed through the additional one capillary 6.

Further a third embodiment of the capillary column unit is described.

Figure 11:
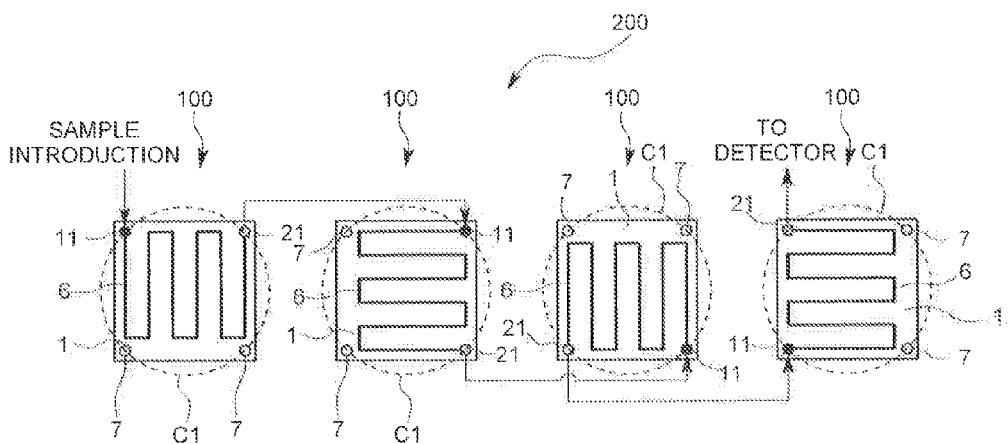
FIG. 11 is a schematic diagram illustrating a shape and flow path example of a plate-type capillary column in a third embodiment of the present invention.
Figure 11:
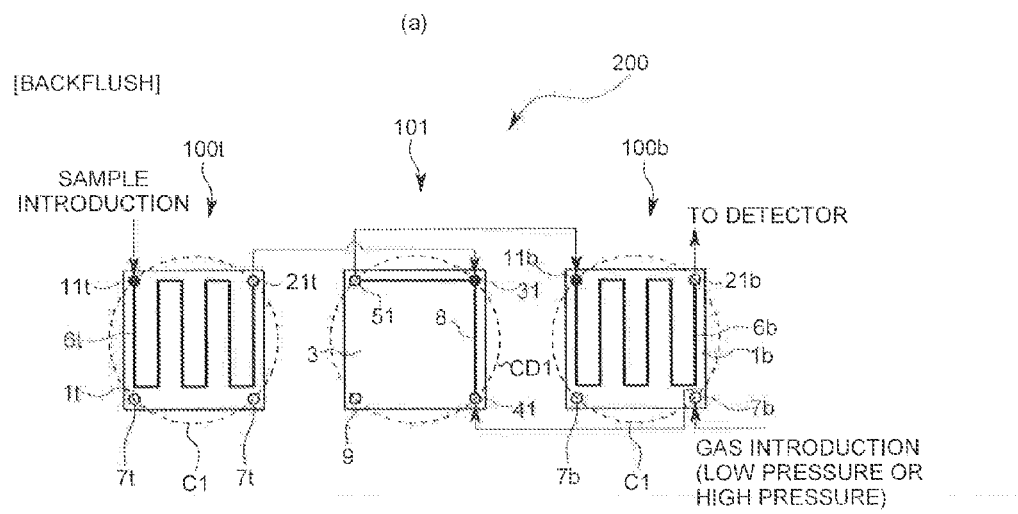

In any of the above-described embodiments, the second bottom-equipped hole 21 and the through-holes 7 are formed with the first bottom-equipped hole 11 formed in the plate P being set as the virtual center; however, the present invention may take other arrangement. Another configuration of the plate-type capillary column 100 is illustrated in FIG. 11. As illustrated in FIG. 11, a plate-type capillary column 100 of the third embodiment is provided with: a plate P having a first face plate part 1 and a second face plate part 2 that face to each other; a capillary 6 that is formed inside the plate P; a first bottom-equipped hole 11 that is connected to one end part of the capillary 6 and formed so as to open in the first face plate part 1; and a second bottom-equipped hole 21 that is connected to the other end part of the capillary 6 and formed so as to open in the second face plate part 2, and characterized in that, as viewed from a direction vertical to the first face plate part 1 or the second face plate part 2, on a capillary column first virtual circle C1, which passes through the first bottom-equipped hole 11 and the second bottom-equipped hole 22, one or more through-holes 7 penetrating through the first face plate part 1 and the second face plate part 2 are formed.

That is, in the plate P, the first bottom-equipped hole 11, second bottom-equipped hole 22, and through-holes 7 are provided on the same capillary column first virtual circle C1, and at the virtual center of the capillary column first virtual circle C1, no hole is formed. That is, in the central parts of first and second plate elements P1 and P2, no through-hole is present, and the only in circumferential parts, the through-holes are present, so that to form the plate P with mutually overlapping the respective plate elements P1 and P2, the circumferential parts are only brought into pressure contact with each other, and thereby airtightness can be easily achieved to eliminate leakage from the first and second bottom-equipped holes 11 and 22 Conversely, as compared with time and effort to contrive a method for joining the respective plate elements P1 and P2 together to join them with preventing leakage in the case where in the central parts, the first bottom-equipped hole 11 is present, in the case where in the central parts, no hole is present as in the third embodiment, the joining can be more easily performed to more easily manufacture the plate-type capillary column 100. Also, in this embodiment, regarding a shape of the capillary 6, too, the capillary 6 having a different shape from that in any of the above-described embodiments is shown as an example.

Even in the case of such a plate-type capillary column 100, as illustrated in FIG. 11(*a*), by stacking the plate-type capillary columns 100 with rotating each of the plate-type capillary columns 100 by 90 degrees with respect to the virtual center, the respective capillaries 6 can be communicatively connected to have an arbitrary length in total. That is, only by preparing the one type of plate-type capillary column 100, a capillary 6 having an arbitrary length can be easily formed as a whole.

Further, as illustrated in FIG. 11(*b*), by preparing a branching flow path board 101 having a different shape from that in the above-described embodiment, for example, a complicated flow path for a backflush can be formed even with such a plate-type capillary column 100. More specifically, in the branching flow path board 101, as viewed from a direction vertical to the third face plate part 3 or the fourth face plate part 4, in the view of FIG. 11(*b*), a third bottom-equipped hole 31 opening only on an upper surface side, a fourth bottom-equipped hole 41 opening only on a lower surface side, a fifth bottom-equipped hole 51 opening only on the lower surface side, and a through-hole 9 formed so as to penetrate between both surfaces are formed on a circumference of the same branching flow path board first virtual circle CD1. Also, a narrow tube 8 is formed so as to position the third bottom-equipped hole 31 at a corner and connect the fourth bottom-equipped hole 41 and the fifth bottom-equipped hole 51 to each other.

Further, a capillary column unit 200 in FIG. 11(*b*) is adapted to communicatively connect the second bottom-equipped hole 21*t* of the upper layer plate-type capillary column 100*t* and the third bottom-equipped hole 31 of the branching flow path board 101 to each other, and also communicatively connect the fifth bottom-equipped hole 51 and the first bottom-equipped hole 11*b* of the lowermost layer plate-type capillary column 100*b* to each other. Still further, the capillary column unit 200 is adapted to communicatively connect the fourth bottom-equipped hole 41 of the branching flow path board 101 and a through-hole 7*b* of the lower layer plate-type capillary column 100*b* to each other, and be able to introduce low or high pressure gas from the through-hole 7*b*. Accordingly, a complicated flow path necessary for the measuring method for a backflush or the like as illustrated in FIG. 8 or 9, which is described in the above embodiment, can be formed with the plate-type capillary column 100 having the one type of shape.

Next, a fourth embodiment of the capillary column unit is described.

In any of the plate-type capillary columns 100 of the first to third embodiments, as viewed from the direction vertical to the first face plate part 1 or the second face plate part 2, only on the capillary column first virtual circle C1, which passes through the second bottom-equipped hole 21, the through-holes 7 penetrating through the first face plate part 1 and the second face plate part 2 are formed; however, in the fourth embodiment, on a capillary column second virtual circle C2 that is a circle concentric with the capillary column first virtual circle, too, through-holes 7 are formed.

That is, a capillary column unit in the fourth embodiment is one that is provided with a configuration for, even in the case of using the plate-type capillary column 100 not provided with the first bottom-equipped hole 11 at the virtual center of the capillary column first virtual circle C1 as in the third embodiment, enabling a complicated flow path like a flow path for heartcutting to be easily formed, too.

Figure 12:
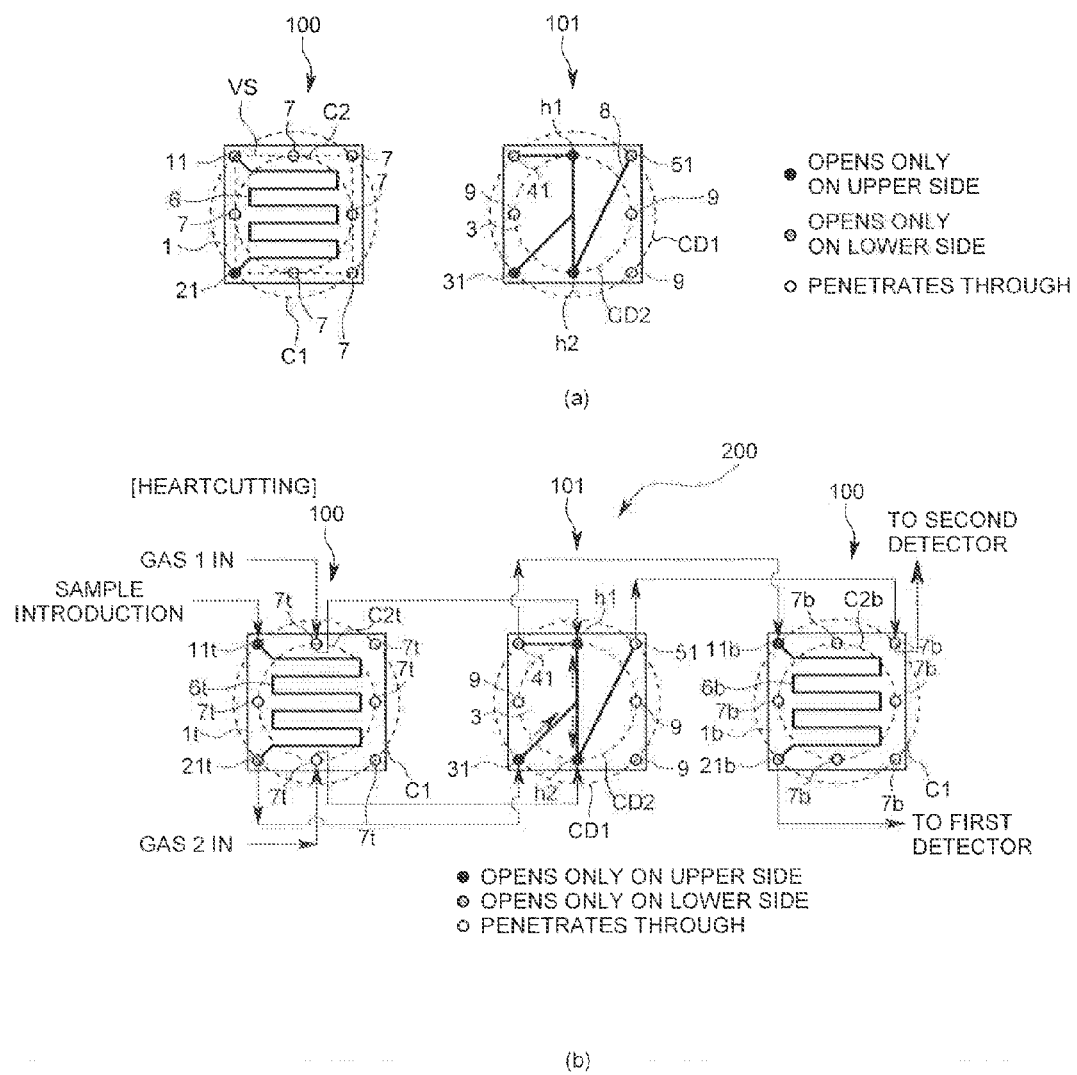
FIG. 12 is a schematic diagram illustrating a shape of a plate-type capillary column and a flow path example for heartcutting in a fourth embodiment of the present invention.

More specifically, as illustrated in FIG. 12(*a*), in the plate-type capillary column 100, the capillary column second virtual circle C2 is one having a diameter smaller than that of the capillary column first virtual circle C1, and on a circumference of the capillary column second virtual circle C2, four through-holes 7 are formed. Further, the through-holes 7 on the capillary column second virtual circle C2 are arranged so as to form a virtual square together with a first bottom-equipped hole 11, second bottom-equipped hole 12, and through-holes 7 present on the capillary column first virtual circle C1. In other words, in a face plate part formed in the squared shape, the respective holes on the capillary column first virtual circle C1 are arranged at the four corners to form vertices of the virtual square, whereas the respective holes on the capillary column second virtual circle C2 are arranged so as to form midpoints of the respective sides of the virtual square. Also, as is clear from FIG. 12(*a*), the respective holes arranged on the capillary column second virtual circle C2 are also arranged so as to be rotational symmetric with respect to the virtual center.

Further, in response to the plate-type capillary column 100 of the fourth embodiment, in a branching flow path board 101, too, on a branching flow path board second virtual circle CD2 corresponding to the capillary column second virtual circle C2, bottom-equipped holes and through-holes are provided.

More specifically, the branching flow path board 101 of the fourth embodiment is, as viewed from a direction vertical to a third face plate part 3 or a fourth face plate part 4, as illustrated in FIG. 12(*a*), provided with a third bottom-equipped hole 31, fourth bottom-equipped hole 41, fifth bottom-equipped hole 51, and through-hole 9 on a branching flow path board first virtual circle CD1 as with the previous embodiment. Further, on the branching flow path board second virtual circle CD2, a sixth bottom-equipped hole h1 provided so as to open in the third face plate part 3, and a seventh bottom-equipped hole h2 opening in the third face plate part 3 are provided. In the fourth embodiment, the sixth bottom-equipped hole h1 forms a midpoint of an upper side of a virtual square, and the seventh bottom-equipped hole h2 forms a midpoint of a lower side of the virtual square. Further, a narrow tube 8 inside the branching flow path board 101 connects the fourth bottom-equipped hole 41 forming an upper left vertex of the virtual square and the sixth bottom-equipped hole h1 to each other, and also connects the fifth bottom-equipped hole 51 forming an upper right vertex of the virtual square and the seventh bottom-equipped hole h2. Still further, the narrow tube 8 starts from the third bottom-equipped hole 31 forming a lower left vertex of the virtual square, and branches on the way, and the branched narrow tubes 8 are respectively connected to the sixth bottom-equipped hole h1 and the seventh bottom-equipped hole h2.

By stacking the plate-type capillary column 100 and branching flow path board 101 configured as described, a flow path for heartcutting can be formed in the fourth embodiment. In the following, a configuration of the flow path for heartcutting in the fourth embodiment is described in detail.

As illustrated in FIG. 12(*b*), the capillary column unit 200 is, from the upper layer, provided side by side with the plate-type capillary column 100*t* of which a first face plate part 1*t* is located on the upper side, the branching flow path board 101 of which the third face plate part 3 is located on the upper side, and the plate-type capillary column 100*b* of which the first face plate part 1*b* is located on the upper side in this order.

The capillary column unit 200 is adapted to introduce a sample from the first bottom-equipped hole 11*t* of the upper layer plate-type capillary column 100*t*, and the sample gas having passed through the capillary 6*t* flows from the second bottom-equipped hole 21*t* to the third bottom-equipped hole 31 of the connected branching flow path board 101. The sixth bottom-equipped hole h1 of the branching flow path board 101 is communicatively connected to the through-hole 7*t* forming the upper side midpoint of the virtual square in the upper layer plate-type capillary column 100*t*. Also, the seventh bottom-equipped hole h2 is communicatively connected to the through-hole 7*t* forming the lower side midpoint of the virtual square in the upper layer plate-type capillary column 100*t*.

Gas 1 and Gas 2 that are respectively different from the sample are introduced into the respective through-holes 7*t*, and by adjusting pressures of the gases, which of the fourth bottom-equipped hole 41 and the fifth bottom-equipped hole 51 the sample gas having passed through the third bottom-equipped hole 31 reaches through the narrow tube 8 can be switched.

In the case of decreasing the pressure of the gas 1 introduced into the sixth bottom-equipped hole h1, and increasing the pressure of the gas 2 introduced into the seventh bottom-equipped hole h2, the sample gas flows to the first bottom-equipped hole 11*b* connected from the fourth bottom equipped hole 41 in the lower layer plate-type capillary column 100*b*. Then, the sample gas passes through the capillary 6*b* and from the second bottom-equipped hole 21*b*, reaches a first detector, where analysis is performed.

On the other hand, in the case of increasing the pressure of the gas 1 introduced into the sixth bottom-equipped hole h1 and decreasing the pressure of the gas 2 introduced into the seventh bottom-equipped hole h2, the sample gas flows to the through-hole 7*b* connected from the fifth bottom-equipped hole 51 in the lower layer plate-type capillary column 100*b*, and reaches a second detector, where analysis is performed.

As described, by adjusting the pressures of the gas 1 and the gas 2, heartcutting-based analysis that can select whether to be performed after the sample gas has passed through the one capillary 6 or after the sample gas has passed through the two capillaries can be realized.

Next, described is the fact that the plate-type capillary column 100 of the fourth embodiment can be used to freely take other flow path configurations.

Figure 13:
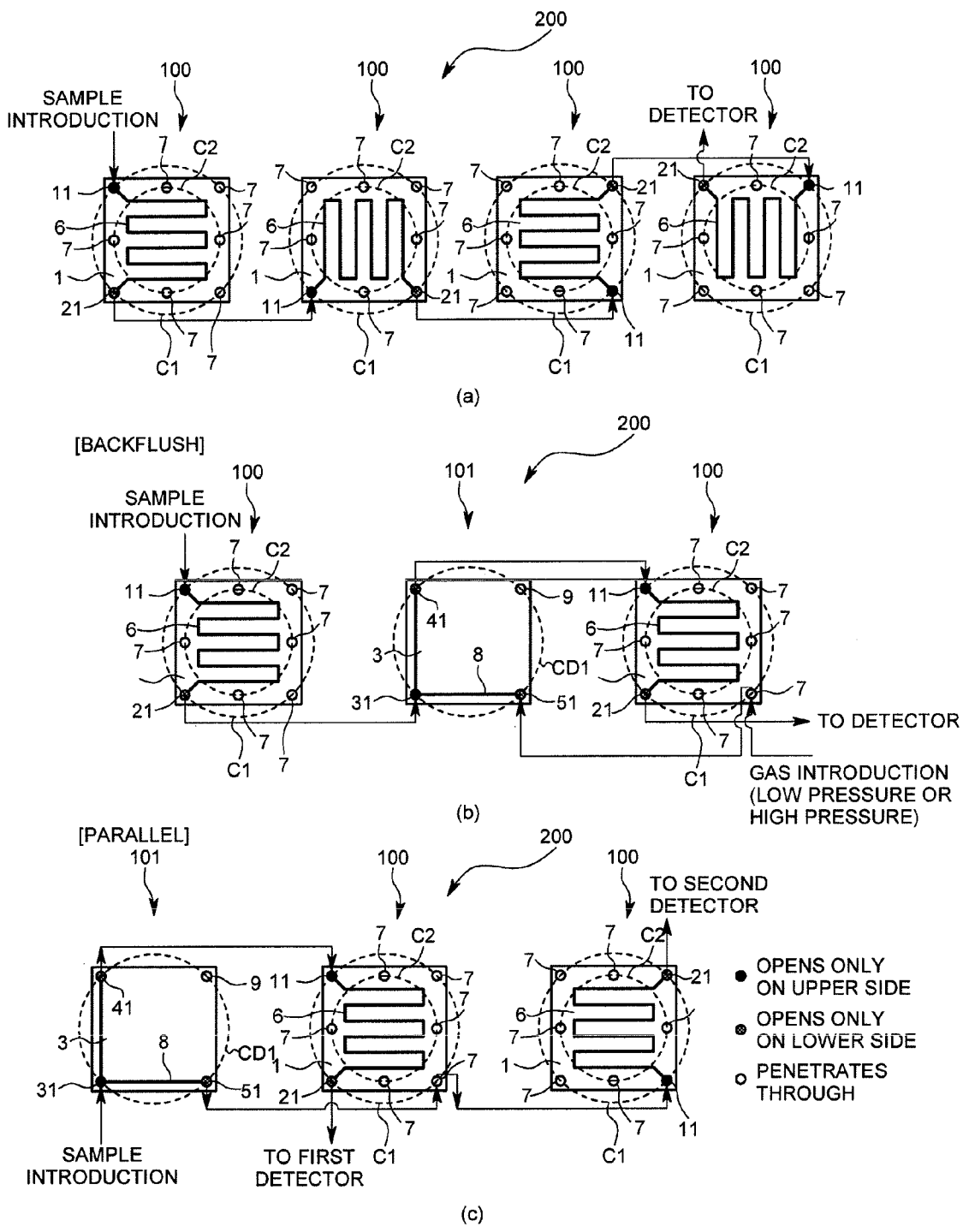
FIG. 13 is a schematic diagram illustrating a various types of flow path configuration examples using the plate-type capillary column in the fourth embodiment.

Similarly to the case illustrated in FIG. 11 and described in the third embodiment, regarding the plate-type capillary column 100 of the fourth embodiment, too, as illustrated in FIG. 13(*a*), by using four plate-type capillary columns 100 to keep connecting the first bottom-equipped hole 11 and the second bottom-equipped hole 12 with rotating each of the plate-type capillary columns 100 by 90 degrees, a capillary 6 having an arbitrary length can be formed as a whole.

Also, by using the branching flow path board 101 illustrated in FIG. 11 and described in the third embodiment, a flow path configuration for a backflush as illustrated in FIG. 13(*b*), or a parallel flow path configuration as illustrated in FIG. 13(*c*) can be realized.

This utilizes the fact that an arrangement configuration of the first bottom-equipped hole 11, second bottom-equipped hole 21, and through-holes 7 arranged on the capillary column first virtual circle C1 in the fourth embodiment is the same as that of the plate-type capillary column 100 in the third embodiment, and also the fact that, as for the parallel and backflush, it is not necessary to use the holes on the capillary column second virtual circle C2.

Further, another embodiment of the branching flow path board 101 is described, which corresponds to the plate-type capillary column 100 of the fourth embodiment.

Figure 14:
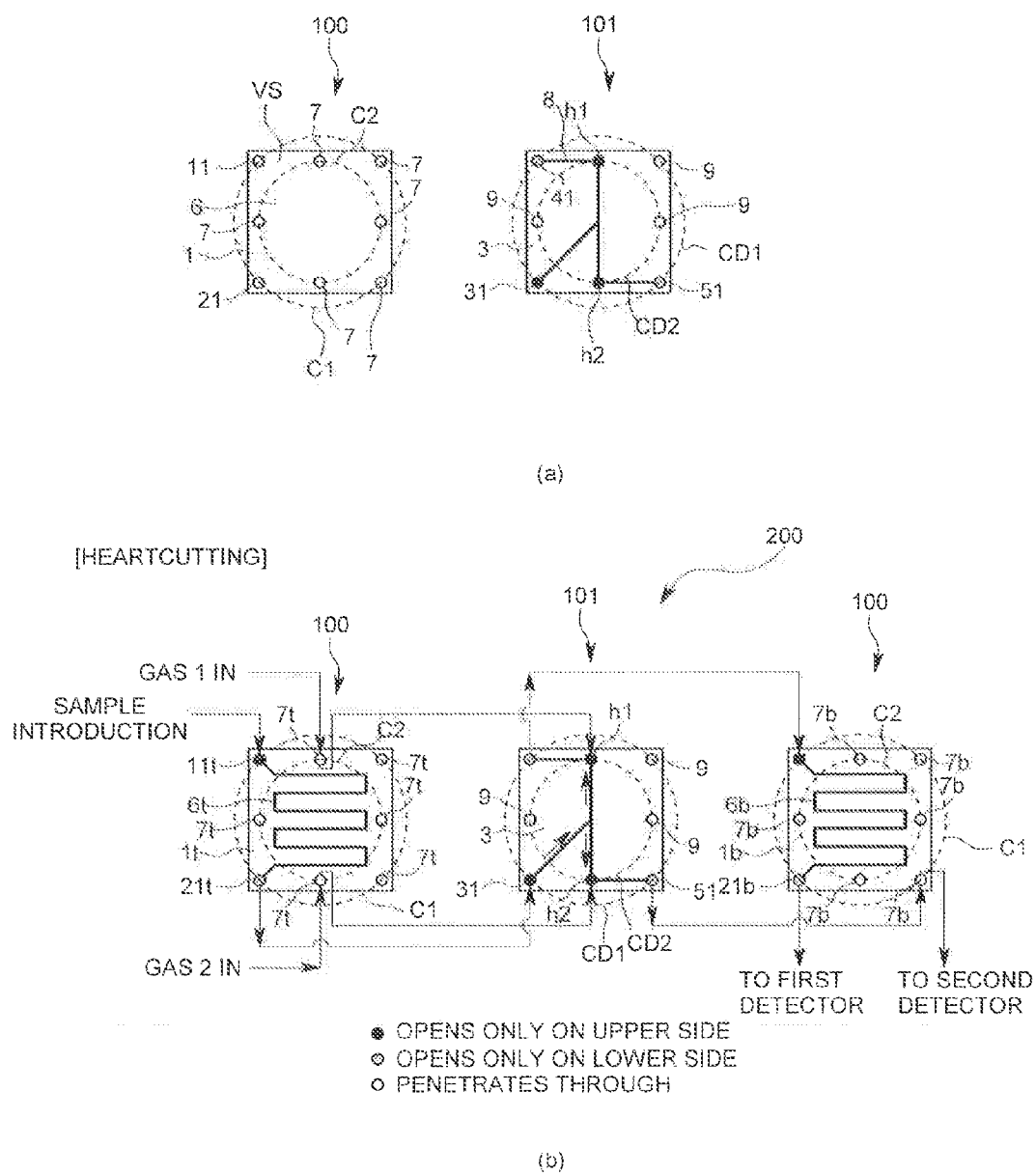
FIG. 14 is a schematic diagram illustrating a configuration example of another branching flow path board in the fourth embodiment.

The branching flow path board 101 is not limited to the above-described one, but may be one that is, as illustrated in FIG. 14(*b*), adapted to have a fifth bottom-equipped hole 51 so as to form a lower right vertex of a virtual square, and connect a seventh bottom-equipped hole h2 and the fifth bottom-equipped hole 51 through a narrow tube 8.

Even with use of the branching flow path board 101 illustrated in FIG. 14(a), similarly to the case illustrated in FIG. 12(b), by connecting respective members, a flow path configuration for heartcutting as illustrated in FIG. 14(b) can be realized.

In addition, to describe a variation of the fourth embodiment, the through-holes 7 present on the capillary column second virtual circle C2 of the plate-type capillary column 100 is not necessarily required to form the virtual square together with the respective holes present on the capillary column first virtual circle C1 and be arranged at the midpoints of the respective sides of the virtual square, but may be arranged at other points on the capillary column second virtual circle C2. Further, similarly, the respective holes present on the branching flow path board second virtual circle CD2 of the branching flow path board 101 may also be arranged at points other than the positions forming the virtual square together with the respective holes on the branching flow path board first virtual circle CD1.

Further, a plate-type capillary column 100 and branching flow path board 101 of a fifth embodiment are described.

Figure 15:
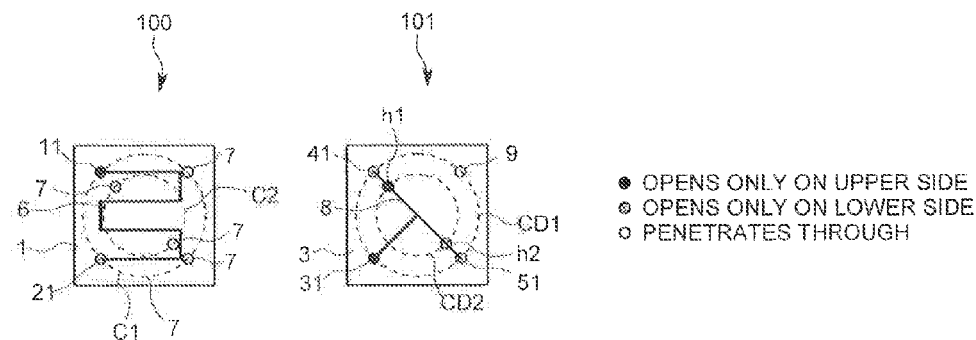
FIG. 15 is a schematic diagram illustrating a shape and flow path configuration of a plate-type capillary column in a fifth embodiment of the present invention.
Figure 15:
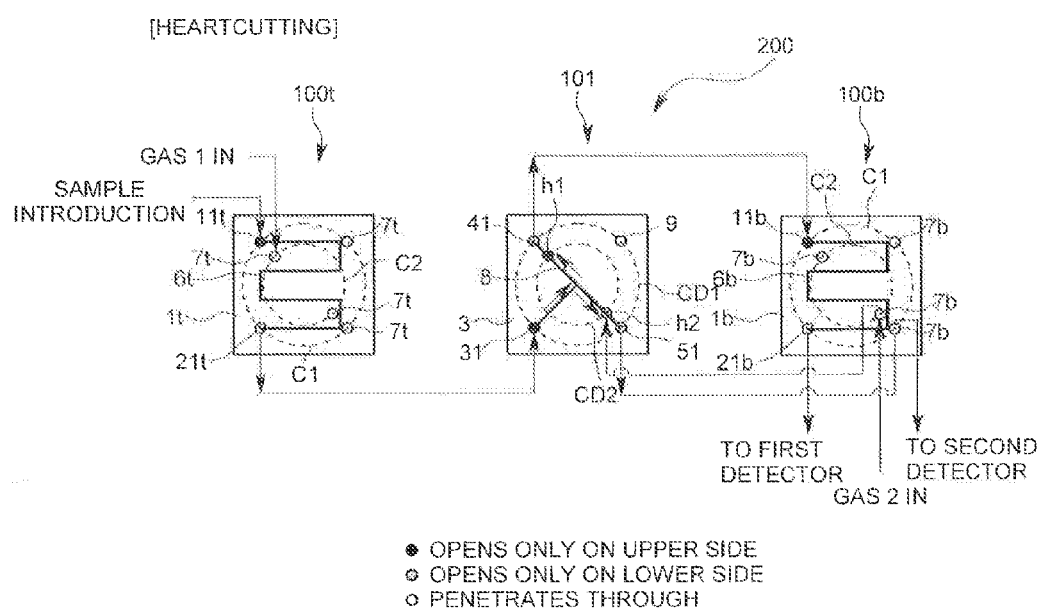

The fifth embodiment is in common with the fourth embodiment in that a plate-type capillary column 100 is provided with through-holes 7 on a capillary column second virtual circle C2, but as illustrated in FIG. 15(a), different in that the capillary column second virtual circle C2 is formed to be smaller in radius than a capillary column first virtual circle C1. Further, a branching flow path board 101 is also configured such that, in the same manner, a branching flow path board second virtual circle CD2 is formed to be smaller in radius than a branching flow path board first virtual circle CD1, and a seventh bottom-equipped hole h2 opens not in a third face plate part 3 but only in a fourth face plate part 4. Also, on the branching flow path board second virtual circle CD2, no through-hole 9 is provided.

Even with such configurations, by stacking based on the same idea as that illustrated in drawings such as FIG. 15(b) in order to make it possible to introduce gas 1 from an upper layer plate-type capillary column 100t, and introduce gas 2 from a lower layer plate-type capillary column 100b as illustrated in FIG. 12(b), a capillary column unit 200 that realizes a flow path configuration for heartcutting can be configured.

In addition, to describe a variation of the fifth embodiment, the variation may be adapted such that respective holes on the capillary column first virtual circle C1 and on the capillary column second virtual circle C2 are not arranged on one straight line, and the through-holes 7 are formed at other positions on the capillary column second virtual circle C2. Similarly, the branching flow path board 101 may also be adapted such that respective holes are not arranged on one straight line, and arranged at other positions on the branching flow path board second virtual circle CD2.

Other embodiments are described.

In each of the above-described embodiments, a shape of the capillary of the plate-type capillary column is a spiral shape or the like; however, any shape other than those illustrated is possible. Also, the number of through-holes penetrating through the respective face plate parts is not limited to four, but may be one or more. In short, it is only necessary to arrange the through-holes on the virtual circle setting the first bottom-equipped hole as the virtual center, or on the virtual circle setting a point other than the first bottom-equipped hole as the virtual center. In the case of setting the first bottom-equipped hole as the virtual center, the virtual center is not necessarily required to coincide with the central axis of the first bottom-equipped hole. For example, even in the case where the virtual center is set anywhere in the first bottom-equipped hole, the virtual center and the central axis may be slightly displaced from each other if at the time of combining the respective plate-type capillary columns, the second bottom-equipped hole can be communicatively connected with a through-hole. In addition, even in the case where on the virtual circle setting not the first bottom-equipped hole but another position as the virtual center, the first bottom-equipped hole, second bottom-equipped hole, and through-holes are arranged, too, even if the virtual centers of the respective plate-type capillary columns are slightly displaced from each other, and at the time of stacking, the respective holes are slightly displaced from corresponding holes, there is no problem if the displacement falls within a range enough to enable communicative connection.

The above-described plate-type capillary column is formed with use of the two plate elements, but may be configured with use of many more plate elements. That is, the present invention may be adapted to form all holes of the plate-type capillary column described in each of the above embodiments as through-holes, and further by attaching cover glass from outside of it, open a first bottom-equipped hole and a second bottom-equipped hole respectively only in a first face plate part and a second face plate part. In other words, a concept of a bottom-equipped hole in the plate-type capillary column of the present invention is not only limited to a bottom-equipped hole formed so as to originally have a bottom but includes a bottom-equipped hole formed by first forming a through-hole and then blocking one of openings.

On the other hand, the plate-type capillary may be one adapted such that inside one plate, a capillary is formed. For example, as a method for forming a capillary inside one plate as described, it is only necessary to set energy at which a first laser, which can change an irradiation position in an X axis direction, and a second laser, which can change an irradiation position in a Y axis direction, can process the plate at a point where the respective lasers intersect with each other, and while appropriately changing the irradiation positions of the respective lasers, excavate the capillary inside the plate.

As the capillary column unit, one that sandwiches, besides the branching flow path board, a heater plate incorporating a heater, or the like, between the plate-type capillary columns is also possible. If so, temperatures inside the capillaries can be kept at optimum temperatures for fulfilling functions as the capillary columns, respectively. Also, in each of the above-described embodiments, the gas chromatograph is taken as an example to provide the description; however, even with a liquid chromatograph, the present invention fulfills a function in the same manner.

Also, in order to make it possible to form a capillary having an arbitrary length by preparing only plate-type capillary columns having the same shape, and only by stacking the plate-type capillary columns with alternately reversing each of the plate-type capillary columns, it is only necessary that each of the plate-type capillary columns is characterized by being provided with: a plate having a first face plate part and a second face plate part that face to each other; a capillary that is formed inside the plate; a first bottom-equipped hole that is connected to one end part of the capillary and formed so as to open in the first face plate part; and a second bottom-equipped hole that is connected to the other end part of the capillary and formed so as to open in the second face plate part. As described, only by, with the first bottom-equipped hole and the second bottom-equipped hole being adapted to open in the different face plates, respectively, and the capillary being formed inside the plate so as to connect the respective bottom-equipped holes to each other, connecting the first bottom-equipped holes of the respective plate-type capillary columns to each other, and connecting the second bottom-equipped holes of the respective plate-type capillary columns to each other, a capillary can be extended as a whole to set the capillary to have a length appropriate for measurement. Further, the capillary is formed inside the plate, so that blocking an opening part of a capillary as in the conventional case where the capillary is formed with opening on a surface of a plate, and at the time of stacking the plates, to keep airtightness inside the capillary, the opening part should be blocked by a surface not formed with the capillary is not required. That is, the plate-type capillary column of the present invention has such features, and therefore a shape thereof can be limited to one type of shape to reduce manufacturing cost because it is not necessary to, as in the conventional technique, alternately change a direction of a bottom-equipped hole or the like that is formed in each of plate-type capillary columns and connected to a capillary, and prepare the plate-type capillary columns respectively having two or more types of shapes.

In each of the above-described embodiments, the radius of the capillary column first virtual circle is equal to or more than the radius of the capillary column second virtual circle; however, the present invention may be one having a reversed radius relationship. The same holds true for a relationship between the branching flow path board first virtual circle and the branching flow path board second virtual circle.

Besides, without departing from the scope of the present invention, various modifications and combinations of the embodiments may be made.

INDUSTRIAL APPLICABILITY

According to the plate-type capillary column, capillary column unit, and chromatograph of the present invention, even without preparing plate-type capillary columns having a number of shapes, a length of a capillary can be freely extended as a whole, and complicated flow path configurations can be realized, so that various measuring methods for chromatographic analysis can be used with manufacturing cost being suppressed.

The invention claimed is:

1. A plate-type capillary column comprising:
a plate having a first face plate part and a second face plate part that face to each other;
a capillary that is formed inside the plate;
a first bottom-equipped hole that is connected to one end part of the capillary and formed so as to open in the first face plate part; and
a second bottom-equipped hole that is connected to the other end part of the capillary and formed so as to open in the second face plate part,
wherein, as viewed from a direction vertical to the first face plate part or the second face plate part, on a capillary column first virtual circle passing through the second bottom-equipped hole, through-holes do not cross the capillary and penetrate through the first face plate part and the second face plate part, and
wherein, as viewed from the direction vertical to the first face plate part or the second face plate part, the first bottom equipped hole is present at a virtual center of the capillary column first virtual circle.

2. The plate-type capillary column according to claim 1, wherein
the second bottom-equipped hole and the respective through-holes are arranged so as to be rotational symmetric around a virtual center of the capillary column first virtual circle.

3. The plate-type capillary column according to claim 1, wherein
the plate includes: a first plate element of which a front surface is formed with a groove; and a second plate element that is attached so as to cover the front surface of the first plate element.

4. A capillary column unit comprising:
the plate-type capillary column according to claim 1; and
a branching flow path board that is stacked on the plate-type capillary column, wherein
the branching flow path board has: a board having a third face plate part and a fourth face plate part that face to each other; a third bottom-equipped hole that is formed so as to open in the third face plate part; a fourth bottom-equipped hole that is formed so as to open in the fourth face plate part; a fifth bottom-equipped hole that opens in any one of the third face plate part and the fourth face plate part; and a narrow tube that is formed in the board so as to connect the third bottom-equipped hole, the fourth bottom-equipped hole, and the fifth bottom-equipped hole to one another, and
in a case of stacking the plate-type capillary column and the branching flow path board on each other with the second face plate part and the fourth face plate part facing to each other, the fourth bottom-equipped hole and the fifth bottom-equipped hole are arranged so as to be communicatively connected to the second bottom-equipped hole and one of the through-holes, respectively.

5. The capillary column unit according to claim 4, wherein
in the branching flow path board, as viewed from a direction vertical to the third face plate part or the fourth face plate part, on a branching flow path board first virtual circle having a same radius as a radius of the capillary column first virtual circle, the fourth bottom-equipped hole and the fifth bottom-equipped hole are formed, and also, on the branching flow path board first virtual circle, one or more through-holes penetrating through the third face plate part and the fourth face plate part are formed.

6. The capillary column unit according to claim 5, wherein
in the branching flow path board, as viewed from the direction vertical to the third face plate part or the fourth face plate part, the third bottom-equipped hole is present at a virtual center of the branching flow path board first virtual circle.

7. The capillary column unit according to claim 5, wherein
in the branching flow path board, as viewed from the direction vertical to the third face plate part or the fourth face plate part, the third bottom-equipped hole is present on the branching flow path board first virtual circle.

8. The capillary column unit according to claim 7, wherein
in the branching flow path board, as viewed from the direction vertical to the third face plate part or the fourth face plate part, on a branching flow path board second virtual circle that is a circle concentric with the branching flow path board first virtual circle and has a same radius as a radius of the capillary column second virtual circle, a sixth bottom-equipped hole that is provided so as to open in the third face plate part, and a seventh bottom-equipped hole that opens in any one of the third face plate part and the fourth face plate part are provided.

9. A capillary column unit in which a plurality of plate-type capillary columns according to claim 1 are stacked, wherein
the respective plate-type capillary columns are stacked such that the first face plate part of one of the plate-type capillary columns is brought into contact with the first face plate part of the other plate-type capillary column, or the second face plate part of one of the plate-type capillary columns is brought into contact with the second face plate part of the other plate-type capillary column, and also the first bottom-equipped hole of one of the plate-type capillary columns is communicatively connected to the first bottom-equipped hole of the other plate-type capillary column, or the second bottom-equipped hole of one of the plate-type capillary columns is communicatively connected to the second bottom-equipped hole of the other plate-type capillary column.

10. A chromatograph using the plate-type capillary column according to claim 1.

11. A plate-type capillary column comprising:
a plate having a first face plate part and a second face plate part that face to each other;
a capillary that is formed inside the plate;
a first bottom-equipped hole that is connected to one end part of the capillary and formed so as to open in the first face plate part; and
a second bottom-equipped hole that is connected to the other end part of the capillary and formed so as to open in the second face plate part,
wherein, as viewed from a direction vertical to the first face plate part or the second face plate part, on a capillary column first virtual circle passing through the second bottom-equipped hole, through-holes do not cross the capillary and penetrate through the first face plate part and the second face plate part, and
wherein, as viewed from the direction vertical to the first face plate part or the second face plate part, the first bottom-equipped hole is present on the capillary column first virtual circle.

12. A plate-type capillary column comprising:
a plate having a first face plate part and a second face plate part that face to each other;
a capillary that is formed inside the plate;
a first bottom-equipped hole that is connected to one end part of the capillary and formed so as to open in the first face plate part; and
a second bottom-equipped hole that is connected to the other end part of the capillary and formed so as to open in the second face plate part,
wherein, as viewed from a direction vertical to the first face plate part or the second face plate part, on a capillary column first virtual circle passing through the second bottom-equipped hole, through-holes do not cross the capillary and penetrate through the first face plate part and the second face plate part, and
wherein, as viewed from the direction vertical to the first face plate part or the second face plate part, on a capillary column second virtual circle that is a circle concentric with the capillary column first virtual circle, one or more through-holes penetrating through the first face plate part and the second face plate part are further formed.

13. The plate-type capillary column according to claim 12, wherein
as viewed from the direction vertical to the first face plate part or the second face plate part, the first bottom-equipped hole, the second bottom-equipped hole, and the through-holes on the capillary column first virtual circle, and the through-holes on the capillary column second virtual circle are arranged so as to form a virtual square.

14. A plate-type capillary column comprising:
at least two stackable plates;
each said stackable plate comprising:
a first plate having an upper side and a lower side;
a second plate having an upper side and a lower side;
the lower side of the first plate facing the upper side of the second plate;
a capillary disposed inside said stackable plate;
a first hole in fluid communication with one end part of the capillary and extending through the first plate;
a second hole in fluid communication with another end part of the capillary and extending through the second plate; and
at least two through holes extending through both the first plate and the second plate and not being in fluid communication with the capillary disposed inside said stackable plate,
wherein the at least two stackable plates are stackable over another so that the at least one through hole of one stackable plate is aligned with the at least one through hole of another stackable plate.

15. The plate-type capillary column of claim 14, wherein the first plate and the second plate are rectangular or square-shaped and the at least two through holes comprises corner openings.

16. The plate-type capillary column of claim 14, wherein each through hole is spaced from the first hole by a same amount as the second hole is spaced from the first hole.

17. A plate-type capillary column comprising:
plural stackable plates stackable atop one another in different rotational positions;
each stackable plate comprising:
a first plate having corners, an upper side and a lower side;
a second plate having corners, an upper side and a lower side;
the lower side of the first plate facing the upper side of the second plate;
a spiral capillary;
a central hole in fluid communication with one end part of the capillary and extending only through the first plate;
a corner hole in fluid communication with another end part of the capillary and extending only through the second plate; and
at least one additional corner hole extending through both the first plate and the second plate and being spaced from the central hole by a same amount as the corner hole; and
at least one additional through hole spaced from the central hole by a different amount that the at least one additional corner hole.

* * * * *